(12) United States Patent
Hielscher et al.

(10) Patent No.: US 9,486,142 B2
(45) Date of Patent: Nov. 8, 2016

(54) MEDICAL IMAGING DEVICES, METHODS, AND SYSTEMS

(75) Inventors: Andreas H. Hielscher, Brooklyn, NY (US); Hyun K. Kim, River Edge, NJ (US); Ludguier D. Montejo, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 651 days.

(21) Appl. No.: 13/993,592

(22) PCT Filed: Dec. 13, 2011

(86) PCT No.: PCT/US2011/064723
§ 371 (c)(1),
(2), (4) Date: Aug. 26, 2013

(87) PCT Pub. No.: WO2012/082789
PCT Pub. Date: Jun. 21, 2012

(65) Prior Publication Data
US 2013/0338496 A1    Dec. 19, 2013

Related U.S. Application Data

(60) Provisional application No. 61/422,536, filed on Dec. 13, 2010, provisional application No. 61/511,009, filed on Jul. 22, 2011.

(51) Int. Cl.
*G06K 9/00* (2006.01)
*A61B 5/00* (2006.01)
(Continued)

(52) U.S. Cl.
CPC .......... *A61B 5/0073* (2013.01); *A61B 5/0064* (2013.01); *A61B 5/0082* (2013.01); *A61B 5/7264* (2013.01); *A61B 6/5211* (2013.01); *G06K 9/6271* (2013.01);
(Continued)

(58) Field of Classification Search
CPC ............. A61B 5/00; G06T 7/00; G06K 9/00
USPC ............. 382/128–134; 378/4, 8, 21–27, 101, 378/901; 600/300, 407, 410, 411, 425, 427
See application file for complete search history.

(56) References Cited

U.S. PATENT DOCUMENTS 7,034,303 B2    4/2006    Schotland et al.
7,148,887 B2    12/2006    Kaufman et al.
(Continued)

OTHER PUBLICATIONS

Gorriz, J. M. et al., "Automatic computer aided diagnosis tool using component-based SVM"—Nuclear Science Symposium Conference Record, 2008, pp. 4392-4395, Published: Feb. 6, 2009.
(Continued)

*Primary Examiner* — Abolfazl Tabatabai
(74) *Attorney, Agent, or Firm* — Potomac Law Group, PLLC; Mark Catan

(57) ABSTRACT

Devices, methods, and systems for providing optical imaging to detect and characterize anatomical and/or physiological indicators, such as, rheumatoid arthritis, and devices, methods and systems for computer aided detection and diagnosis of tomographic images. Embodiments for optimizing machine classification of tissue samples are described. Embodiments for using machine classification techniques to classify indicators present in optical tomographic images are described.

31 Claims, 13 Drawing Sheets

(51) Int. Cl.
*G06K 9/62* (2006.01)
*G06T 7/00* (2006.01)
*A61B 6/00* (2006.01)
*A61B 5/05* (2006.01)

(52) U.S. Cl.
CPC .......... *G06K 9/6278* (2013.01); *G06T 7/0012* (2013.01); *A61B 5/7267* (2013.01); *G06T 2207/10101* (2013.01); *G06T 2207/20081* (2013.01); *G06T 2207/30008* (2013.01)

(56) References Cited

U.S. PATENT DOCUMENTS

| | | | |
|---|---|---|---|
| 7,203,354 B2* | 4/2007 | Wilson | G06T 7/0083 382/131 |
| 7,272,264 B2 | 9/2007 | ElShishiny et al. | |
| 7,463,362 B2 | 12/2008 | Lasker et al. | |
| 7,551,950 B2 | 6/2009 | Cheng | |
| 7,728,986 B2* | 6/2010 | Lasker | G01N 21/4795 356/479 |
| 7,760,941 B2 | 7/2010 | Bornemann et al. | |
| 2003/0137669 A1 | 7/2003 | Rollins et al. | |
| 2004/0052328 A1 | 3/2004 | Sabol et al. | |
| 2004/0221855 A1* | 11/2004 | Ashton | G06F 19/363 128/898 |
| 2005/0283071 A1 | 12/2005 | Ripoll et al. | |
| 2006/0187533 A1 | 8/2006 | Nielsen et al. | |
| 2008/0009722 A1* | 1/2008 | Simopoulos | A61B 8/08 600/437 |
| 2008/0173093 A1* | 7/2008 | Wang | A61B 5/0073 73/602 |
| 2009/0247847 A1 | 10/2009 | Pogue et al. | |
| 2010/0081922 A1 | 4/2010 | Schipper | |
| 2010/0262015 A1 | 10/2010 | Ntziachristos | |
| 2010/0265493 A1 | 10/2010 | Jiang et al. | |
| 2011/0124947 A1* | 5/2011 | Kuo | A61K 49/0002 600/2 |

OTHER PUBLICATIONS

Chaves, R. et al., "SVM-based computer-aided diagnosis of the Alzheimer's disease using t-test NMSE feature selection with feature correlation weighting"—Neuroscience Letters, vol. 461, Issue 3, pp. 293-297, Published: Sep. 15, 2009.

Netz, Uwe et al., "Multipixel system for gigahertz frequency-domain optical imaging of finger joints"—Review of Scientific Instruments, vol. 79, issue 3, 2008.

Klose et al., Multiparameter classifications of optical tomographic images. Journal of Biomedical Optics, Sep./Oct. 2008, vol. 13(5) retrieved from SPIE Digital Library.

Hiltunen et al., A combined reconstruction-classification method for diffuse optical tomography. Institute of Physics and Engineering in medicine, 2009 retrieved from the internet.

Bouktif et al., Improving Rule Set Based Software Quality Prediction: A genetic algorithm-based approach. Journal of Object Technology, vol. 3, No. 4, Apr. 2004, Special issue: Tools USA 2003, retrieved from the internet.

Yalavarthy P., A generalized least-squares minimization method for near infrared diffuse optical tomography. Dartmouth College 2007. Retrieved from ProQuest Dissertations and Theses.

Klose et al., Investigations of RA-Diagnostics applying Optical Tomography in frequency-domain. SPIE vol. 3196, 1998.

* cited by examiner

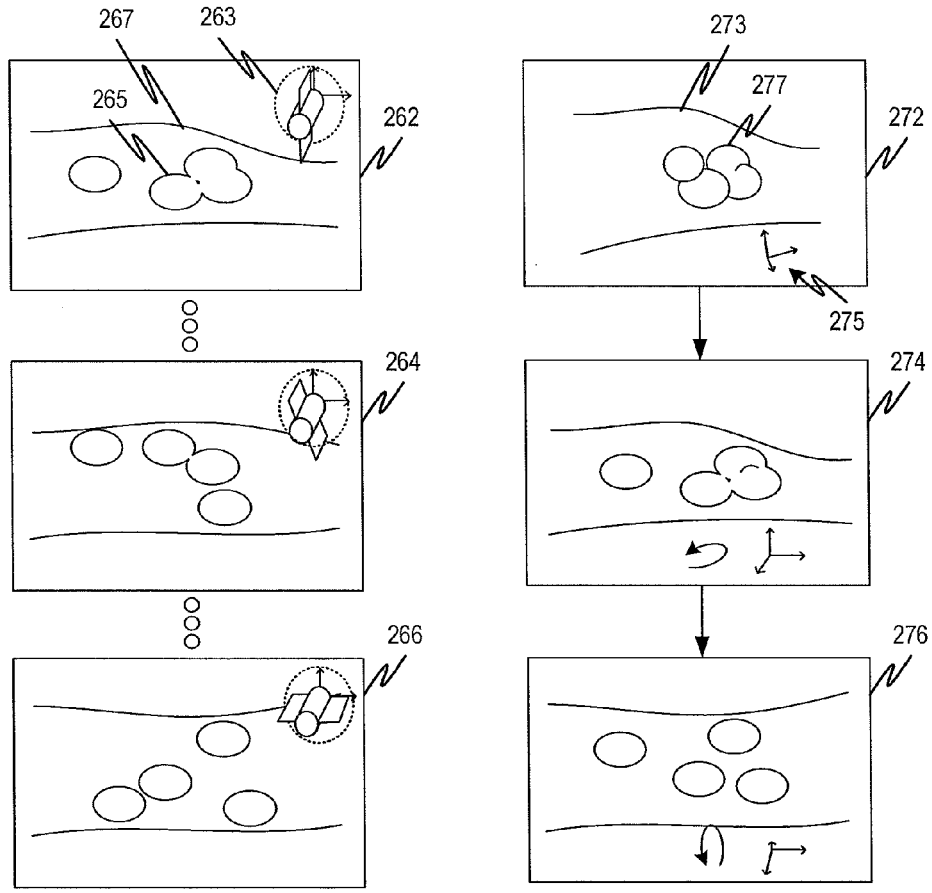
Fig. 2C
Fig. 2D
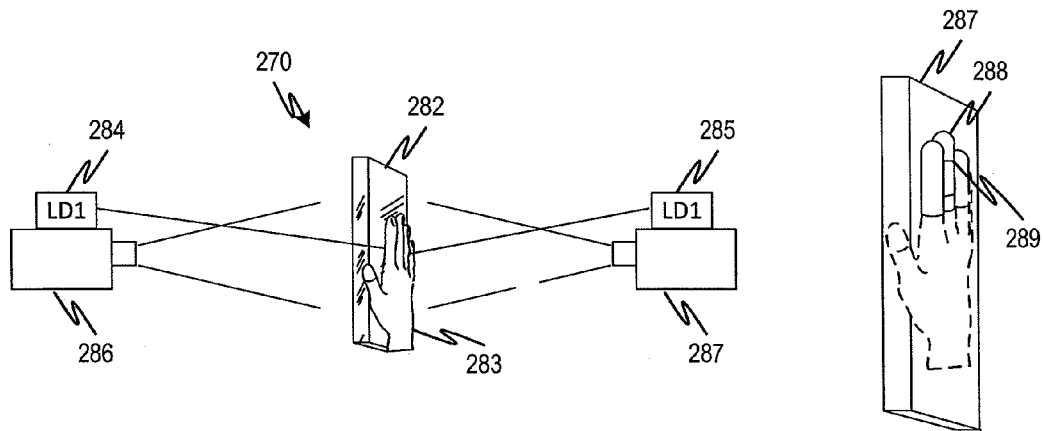
Fig. 2E
Fig. 2F

Absorption coefficient distributions in PIP joints

Healthy　　　　　　Affected　　　　　　Ambiguous

Scatterong coefficient distributions in PIP joints

Healthy　　　　　　Affected　　　　　　Ambiguous

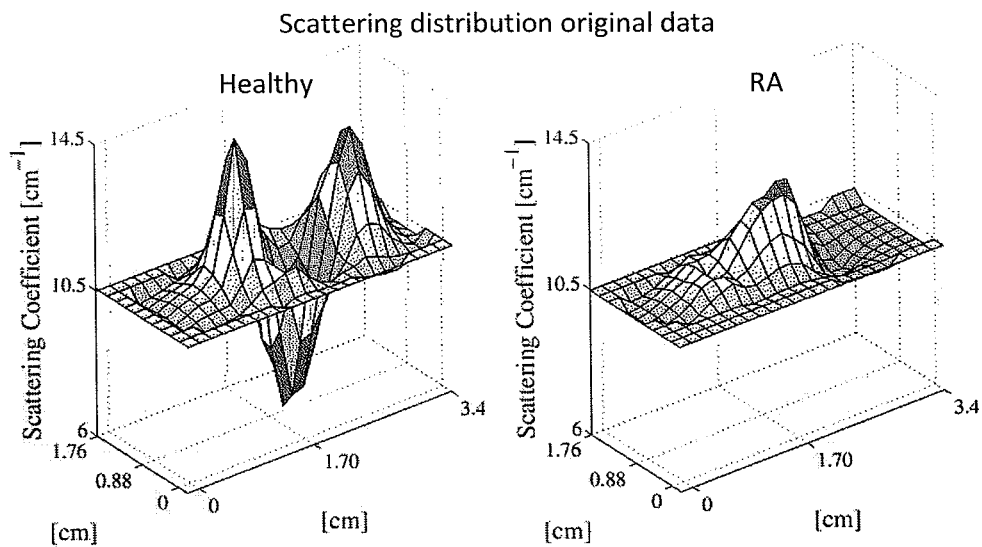
Fig. 5A  Fig. 5B
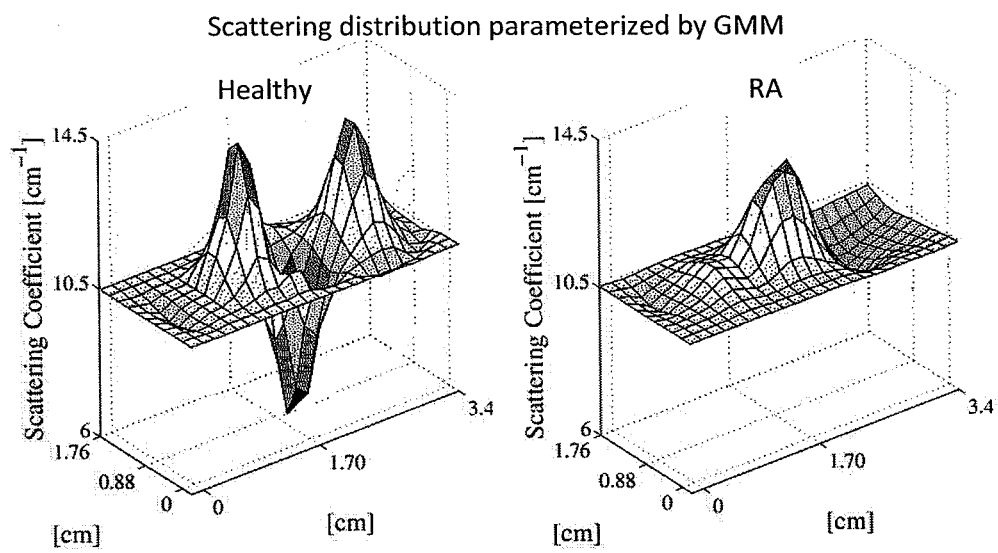
Fig. 5C  Fig. 5D

(a)

(b)

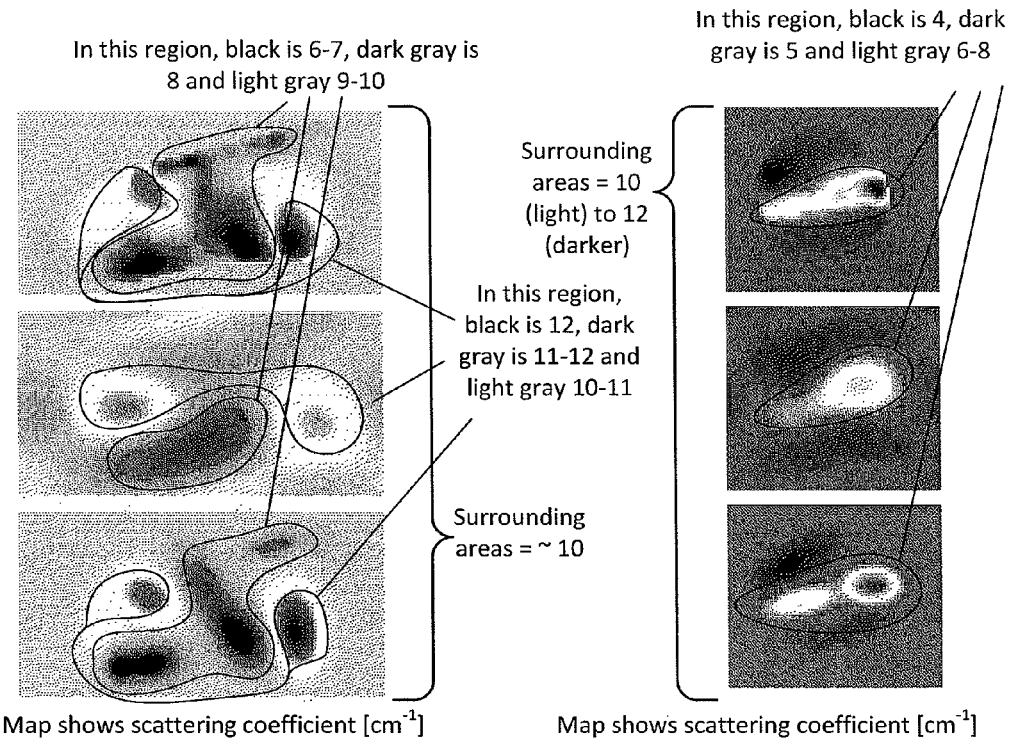
Fig. 9A  Fig. 9C
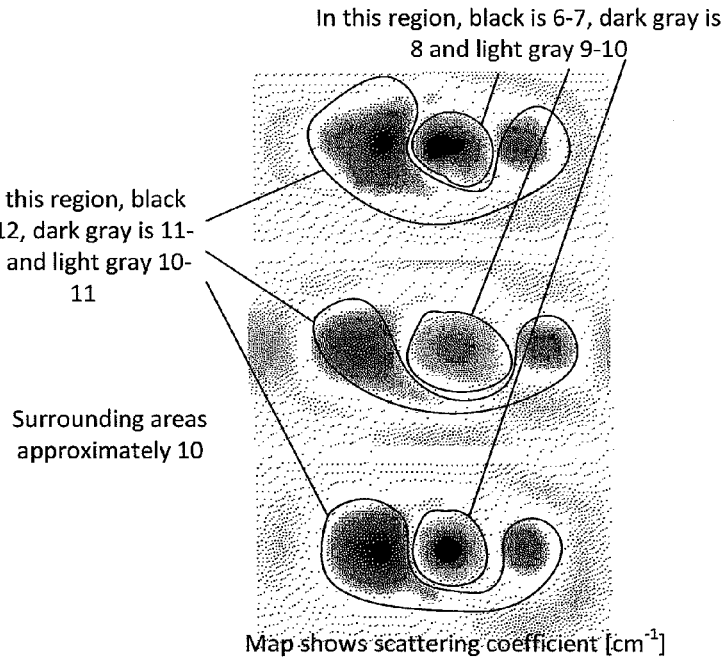
Fig 9B

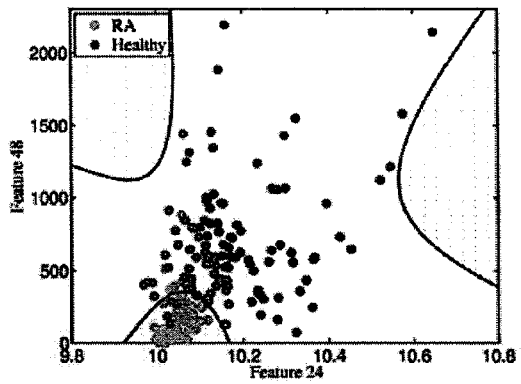 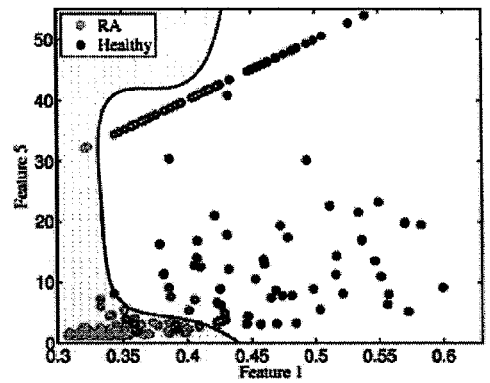
Fig. 14 (a)  Fig. 14 (b)
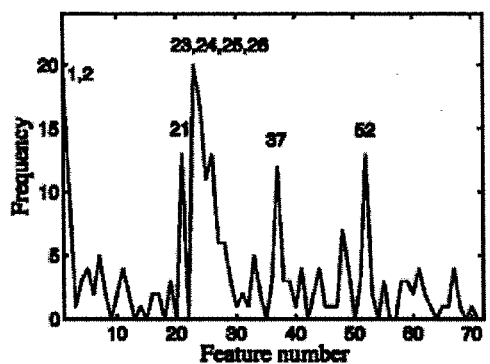 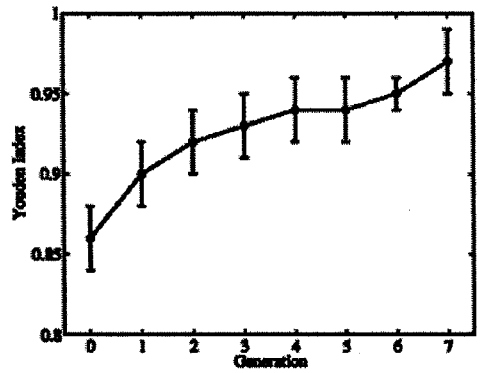
Fig. 14 (c)  Fig. 14 (d)
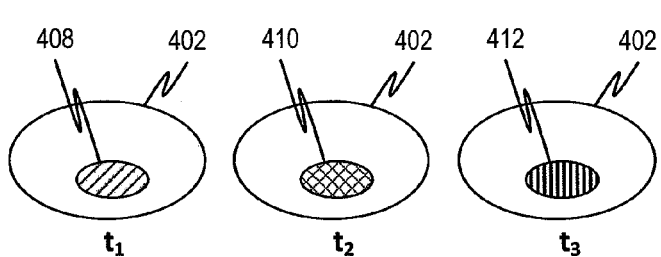
Fig. 15A
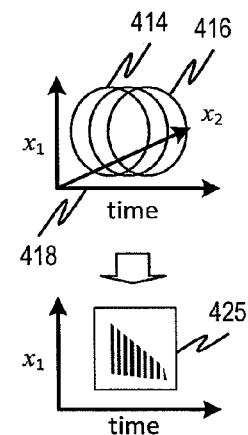
Fig. 15B

MEDICAL IMAGING DEVICES, METHODS, AND SYSTEMS

CROSS-REFERENCE TO RELATED APPLICATIONS

The present application is an International (PCT) application, which claims the benefit of U.S. Provisional Application No. 61/511,009, filed Jul. 22, 2011, and U.S. Provisional Application No. 61/422,536, filed Dec. 13, 2010, both of which are incorporated herein by reference in their entireties.

STATEMENT REGARDING FEDERALLY SPONSORED RESEARCH OR DEVELOPMENT

This invention was made with government support under AR046255 awarded by the National Institutes of Health (NIH). The government has certain rights in the invention.

FIELD

The present disclosure relates to medical imaging, and more specifically to devices, methods and systems for providing optical imaging to detect and characterize anatomical or physiological indicators, such as, rheumatoid arthritis, and to devices, methods and systems for computer aided detection of such indicators, discrimination and classification of physiological and anatomical features, and diagnosis. The technology may be applied to tomographic images for which the technology has been demonstrated as an aid in the detection of rheumatoid arthritis (RA).

BACKGROUND

Various imaging medical modalities are known, including radiography, computed tomography, magnetic resonance imaging, optical tomography, nuclear imaging, thermography, ultrasound, low coherence interferometry. Systems have been described for processing a medical image to automatically identify the anatomy, physiology, and view from the medical image. Machine leaning has been described in the medical imaging field, including medical image analysis and computer-aided diagnosis. Medical pattern recognition systems have been described that learn from examples. Classification of features such as cancerous tumors based on pattern recognition in raw and reduced (segmented and derived features) image data has been described. The technology holds great promise and there is a continuing need for further development.

The present application describes imaging systems in terms of the example modality of diffuse optical tomography (DOT) applied to early detection of rheumatoid arthritis although many aspects of the disclosed subject matter are applicable to other imaging modalities and physiological and anatomical and/or physiological features or conditions. DOT has many benefits including lack of ionizing radiation, avoidance of the need for contrast agents, cost, size, and contact-free acquisition.

In previous studies relating to the application of optical tomographic imaging for detecting and characterizing inflammation in rheumatoid arthritis (RA), it has been observed that absorption coefficients $\mu_a$ and the scattering coefficient $\mu_s$ inside and adjacent to the joint cavity are elevated in patients with RA compared to healthy subjects. However, using a single optically derived parameter (for example the smallest or the largest absorption coefficient, $\min(\mu_a)$ or $\max(\mu_a)$), for classification, sensitivities (Se) and specificities (Sp) of only 0.71 were achieved. Subsequent studies showed that using a continuous wave (CW) instrument to measure the amplitude of transmitted light intensities and combining optically derived parameters, such as $\max(\mu_a)$ and $\min(\mu_a)$, sensitivities and specificities can be increased to 0.76 and 0.78, respectively. However, CW systems have difficulties separating absorption and scattering effects, which then limit the achievable sensitivities and specificities.

SUMMARY

According to embodiments, the present disclosure describes a frequency-domain imaging system to image body parts, such as but not limited to, fingers, at selectable and multiple modulation frequencies. According to embodiments, the present disclosure further includes systems, devices and methods for implementing computer-aided diagnosis techniques for diagnosing disease, such as, but not limited to, RA, from optical tomographic images.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIGS. 2C and 2D illustrate user interfaces for interactively selecting orientations for accepting regions of interest and/or image planes.

FIGS. 2E and 2F show devices for generating surface geometry and optical tomographic data.

FIGS. 5A through 5D show scattering maps including data for a healthy subject and for a subject with RA as original distributions and as represented by surface fit such as Gaussian mixture model (GMM).

FIGS. 9A, 9B, and 9C present sample results from data projection, parameterization, and spectral analysis.

FIG. 14(a) shows SVM decision boundaries for optimal separation between features extracted from RA affected and healthy finger joints, respectively.

FIG. 14(b) is a polynomial kernel of order 5 decision boundary for certain features.

FIG. 14(c) shows frequency with which all features appeared as optimal classifiers.

FIG. 14(d) shows an evolution path of an objective function for a winning feature combination.

FIGS. 15A and 15B show the evolution of a spatial distribution of a physiological property over time in an imaged body part.

DETAILED DESCRIPTION

Figure 1:
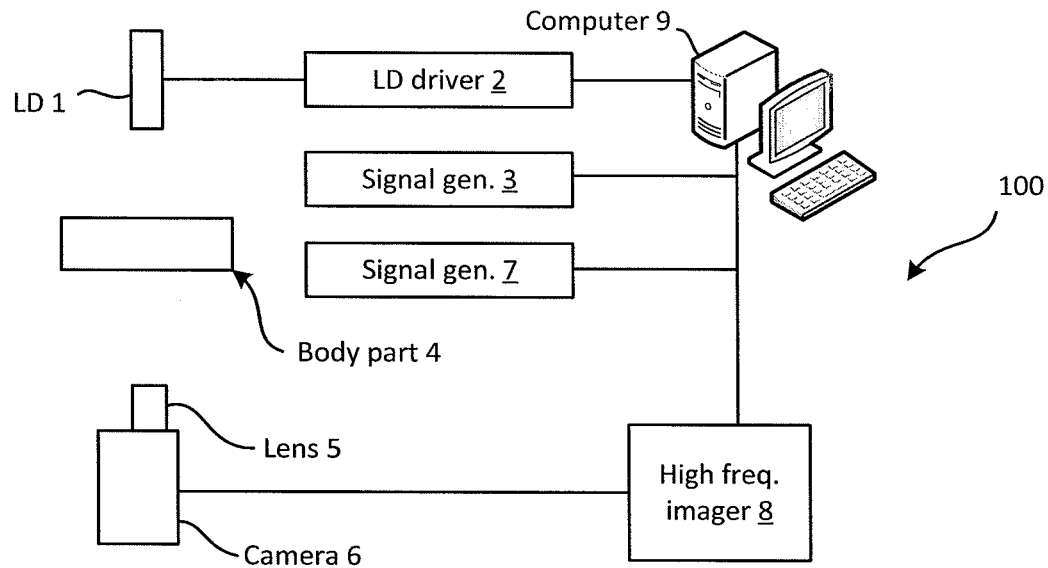
FIG. 1 illustrates a tomographic imaging system to generate optical tomographic, cross-section, volumetric and planar projection transmission data of a body part of a patient according to embodiments of the disclosed subject matter.

FIG. 1 illustrates a frequency-domain tomographic imaging system 100 that can be used to generate a plurality of optical tomographic cross-section and volumetric images, as well as raw tomographic transmission data of a body part of a patient. The system 100 may also be used to generate surface models of the body part of a patient. The system 100 facilitates source-modulation frequencies for up to 1 GHz. For example, modulation frequencies of 400 MHz to 800 MHz, and preferably, frequencies of 400 MHz to 600 MHz, can be used. The system 100 can include a laser source LD 1, such as, but not limited to a laser diode, a laser diode driver 2, signal generators 3 and 7, a body part (finger, foot, breast, etc.) placement area 4 for surface scans as well as trans-illuminating imaging of the body part, one or more lenses 5, an ICCD camera 6, a high frequency imager 8, and a computer processing system 9. The ICCD camera 6 is preferably operated in homodyne mode, i.e. the gain of the ICCD 6 can be modulated by a slave signal generator at the same frequency as the laser. As a result, a steady state image at the intensifier output can be imaged to the ICCD 6. The signal in the detector pixels can depend on the phase between the laser diode LD 1 source and detector modulation. Master and slave signal generators can be linked together and the phase delay can be made adjustable.

To detect the modulated transmitted and scattered light, multiple images may be acquired at phase delays covering the range of $2\pi$ to be transferred to the computer processing system 9. From the stack of generated images, two-dimensional amplitude and phase images can be derived by data processing in the computer processing system 9. The computer processing system 9 may further include a user interface, including a keyboard for data entry, a pointing device such as a mouse, a display device, etc., as well as programming for controlling both the hardware and software and to enable the computer processing system 9 to interact with a user. The programming may include software for implementing the device drivers, operating systems, and user applications.

Figure 2A:
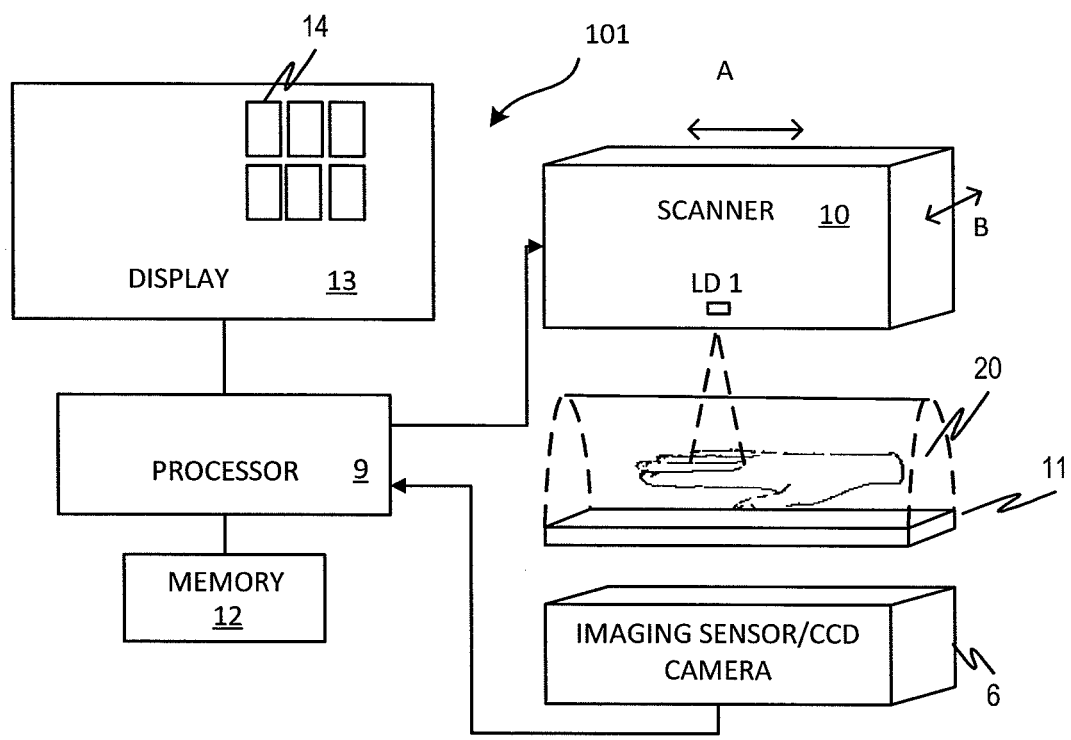
FIG. 2A shows an imaging system with a scanning mechanism for scanning the laser light from the laser diode LD 1 onto a body part according to embodiments of the disclosed subject matter.

FIG. 2A shows the imaging system 101 further including a scanning mechanism 10 for scanning laser light from a laser diode LD 1 onto a body part, such as a hand, and more particularly, a finger 20 of a patient, to generate a plurality of tomographic images of one or more of the patient's fingers 20. The hand of the patient can be positioned in a hand resting mechanism 11, which can be a glove-like holding device positioned in the body part placement area 4, in between a scanning mechanism 10 and an imaging device 6, so that, prior to the commencement of the scanning, the patient can insert his/her fingers 20 into the glove-like holding device 11 with the palm facing toward the imaging device 6. The glove-like holding device 11 keeps the fingers 20 of the patient stationary during the scanning. The shape of the holding device 11 is not limited to a glove-like shape or the body part to fingers but may relate to other body parts such as foot, other limbs, breast, etc. The imaging device 6 may be a CCD camera or other suitable imaging device.

The laser scanning mechanism 10 may scan the light from one or more frequency-modulated laser beam sources LD 1 across the back side (i.e., the side opposite the palm) of the patient's fingers 20 so that the light is scanned across the PIP joints in the fingers. Both the scanning mechanism 10 as well as the imaging device 6 can be moved independently in a plurality of directions (A, and B, for example), so that images in a plurality of imaging planes, such as, but not limited to, the transverse, sagittal, and coronal planes, can be generated. For example, the frequency-modulated laser beam can selectively or collectively scan the back of each finger, stopping at a plurality (e.g., eleven) of discrete locations to allow for data acquisition. Trans-illumination data can be recorded from each source position at the front (i.e., the palm side) of each finger with the intensified CCD camera (ICCD) 6. The trans-illumination data captured by the CCD camera 6 is then sent to the computer processing system 9 (e.g., microprocessors, microcontroller, etc.) coupled to the CCD camera 6 for image reconstruction and processing.

In addition to the transmission measurements, accurate surface coordinates of the fingers 20 can also be generated using the same laser scanning mechanism 10 or a separate laser scanning mechanism, essentially as shown in FIG. 2A but which is arranged to capture light reflected from the laser by the body part so as to acquire surface geometry. For example, the fingers 20 can be scanned simultaneously by two laser lines generated by one or two diode lasers LD 1 and LD 2 (not shown) emitting light 9 for example, having wavelengths $\lambda$=650 nm, optical power=5 mW, and line widths 0.2 mm). The diode lasers or optical components such as mirrors or prisms can be mounted on traversal mechanisms for scanning. A dot pattern of a pulsed laser or the shapes of the deformed laser lines on the finger surface can be acquired to form an image of the surface of the body part. Gauges can also be arranged near the position of the body part to serve as a calibration background to adjust the coordinate system of the camera. According to the second camera coordinate system, the line shapes can be transformed into three-dimensional (3D) surface coordinates in real-time. These coordinates can then be used to generate a 3D surface mesh of the scanned part of the finger using GID software package, which can also be input into the image reconstruction procedure together with the transmission data.

In operation, prior to commencing the tomographic measurements, the body part can be registered with respect to the imaging apparatus. For example, fingers 20 can be marked with a small black dot on the back of the finger in the sagittal plane, e.g., 17 mm distal from the PIP joint. This exemplary mark can be used to position the finger 20 in the scanning mechanism 10 prior to acquiring tomographic images, and prior to acquiring surface coordinates, as well as to position the finger 20 into the second scanning mechanism when a separate scanning mechanism is used for acquiring the surface coordinates. Other fiducial markers may be used. Alternatively a mechanism that conforms precisely to the body part or forces conformation of the body part to it may be used. For example the system may accommodate a supporting device with a custom fitting member in contact with the body part.

In the present example, once the finger is placed inside the hand resting device 11, the laser beam may be moved to the marked position. The finger axis can be aligned with the scanning plane of the laser source LD 1. The laser is then moved to the first tomographic source position, e.g., 10 mm distal from the PIP joint, for example. The laser is moved over a range, and images can be acquired at equally spaced source positions, for example. In an exemplary embodiment, the laser can be moved over a range of about 20 mm, and the images can be acquired at about 11 spaced source positions. At each source position, the oscillation can be sampled in phase steps with a predetermined exposure time. In an exemplary embodiment, this can be performed in, e.g., 16 phase steps with an exposure time of 80 ms each. For example, the scan can be performed twice, at first in forward direction with modulation frequency of about 600 MHz, then the frequency can be switched to about 300 MHz and the scan can be repeated backwards. The number of iterations of the scans can be varied depending on the specific application.

An additional laser line can be used across the finger as a pilot beam to assist in locating the correct axial position for the mark. In one embodiment, the finger 20 can be angled parallel to the scanning direction A. The exemplary scan can start before the mark and can end after a particular distance on both sides of the mark. In one exemplary embodiment, the scan can start at approximately 3 mm before the mark and can end at after a distance of approximately 40 mm. In another exemplary embodiment, one step of the stepping motor can facilitate a step of the laser line on the finger surface of approximately 0.05 mm and can take about 10 ms. Both, the imaging camera 6 and the second scanning camera (shown in FIG. 2A) can be in a free running mode and take images at 30 frames per second, for example. To get approximately one step per frame, a waiting time of about 20 ms can be inserted between the steps. The scanning over about 40 mm can take about 25 seconds, and the positioning averages another 60 seconds. Thus, the complete time for scanning five fingers using this exemplary embodiment can be about 7 minutes.

FIGS. 2E and 2F show devices for generating surface geometry and optical tomographic data. FIG. 2E shows an imaging system 270 that includes scanning lasers 284 and 285 and imaging devices 286 and 287 disposed on respective sides of a transparent body part support 282. The body part support 282 may be configured to support a hand 283 or any other body part. The body part can be positioned on the support 282. In an embodiment, as shown in FIG. 2F, the support 287 has a holding mechanism 288 that holds the body part in position. The holding mechanism 288 may be a fixed conforming fixture such as one in the shape of glove fingers as shown at 2888 attached to the support 287 so as to constrain the body part. The fixture may have resilient or non-resilient features to hold the body part in place. A window 289 may be provided. In the embodiment shown, the user may insert his/her fingers into the holding mechanism before scanning. The scanning mechanism may scan light from the two lasers 284 and 285 across the body part to acquire surface geometry before, after, or during an OT scan using the other laser 284. Here the geometry of the body part may be defined in part by the shape of the support 282 so that only surface scanning data needs to be acquired by imaging device 287.

Other features may be as disclosed with respect to FIG. 2A. For example, the cameras and or lasers may be moved automatically under control of a signal acquisition system that is programmed to perform the OT and surface scanning operations. While one imaging device captures emitted light from the body part, the other may capture surface geometry. The interference between the two processes may be eliminated or reduced by time division multiplexing or using lasers of different wavelength with respective wavelength filters on the imaging devices.

Once the generating of the trans-illumination measurements is completed, the image data is further processed in the computer processing system 9, which reconstructs tissue absorption and scattering coefficient distributions, as optical parameters. The optical parameters can be reconstructed using a PDE-constrained optimization algorithm, where the equation of radiative transfer equation (ERT) can be used to model propagation of near infrared (NIR) light in tissue, for example.

According to an embodiment, three dimensional image reconstructions can be performed using the PDE-constrained reduced Hessian SQP method that solves the forward and inverse problems simultaneously. As a forward model this procedure employs by the frequency-domain equation of radiative transfer (FD-ERT)

$$(\nabla \cdot \Omega)\psi(\vec{r}, \Omega, \omega) + \left(\mu_a + \mu_s + \frac{i\omega}{c}\right)\psi(\vec{r}, \Omega, \omega) = \frac{\mu_s}{4\pi}\int_{4\pi}\psi(\vec{r}, \Omega', \omega)\Phi(\Omega, \Omega')d\Omega' \quad (1)$$

where $\psi(\vec{r}, \Omega', \omega)$ is the complex-valued radiance in unit [W/cm$^2$/sr.], $\mu_a$ and $\mu_s$ are the absorption and scattering coefficients, respectively, in units of [cm$^{-1}$], $\omega$ is the external source modulation frequency and c is the speed of light inside the medium, $\Phi(\Omega,\Omega')$ is the scattering phase function that describes scattering from incoming direction $\Omega'$ into scattering direction $\Omega$. For example, the Henyey-Greenstein phase-function with g=0.9 can be used.

Further, to enable consideration of the refractive index mismatch at air-tissue interface, a partially-reflective boundary condition may be implemented. An example boundary condition is as follows:

$$\psi_b(\vec{r}_b,\Omega,\omega)|_{\vec{n}_b\cdot\Omega<0} = \psi^0(\vec{r}_b,\Omega,\omega) + R(\Omega,\Omega')\cdot\psi_b(\vec{r}_b,\Omega',\omega)|_{\vec{n}_b\cdot\Omega'>0} \quad (2)$$

where $R(\Omega,\Omega')$ is the reflectivity at Fresnel interface from direction $\Omega'$ to direction $\Omega$, $\psi^0(\vec{r}_b,\Omega,\omega)$ is the radiation intensity due to the external source function and subscript denotes the boundary surface of the medium, while $\vec{n}_b$ is the unit normal vector pointing outwards the boundary surface. Other approximations are also possible.

Given the spatial distribution of optical properties inside the medium, the radiative transfer equation (1) may be solved with a discrete ordinates method, which can provide the prediction of measurements obtained on the surface of the medium $P_{d,s}(\vec{r}_b,\omega)=Q_d\psi_s(\vec{r}_b,\Omega,\omega)$. For example, $Q_d$ is the measurement operator that projects the radiance vector $\psi_s(\vec{r}_b,\Omega,\omega)$ of a forward model onto the image plane of the imaging device.

In PDE-constrained optimization, an exemplary image reconstruction problem is to find the radiation intensity vector $$\psi=(\psi^1,\psi^2,\ldots,\psi^m) \quad (3)$$

and the optical property vector $$\mu=(\mu_a^1,\mu_a^2,\ldots,\mu_a^n,\mu_s^1,\mu_s^2,\ldots,\mu_s^n) \quad (4)$$

such that $$\min \; f(\mu,\psi) = \frac{1}{2}\sum_{s=1}^{N_s}\sum_{d=1}^{N_d}(Q_d\psi_s - z_{s,d})(Q_d\psi_s - z_{s,d})^* \quad (5)$$

$$\text{s.t.} \; A(\mu_a,\mu_s)\psi_s = b_s; s=1,\ldots,N_s$$

where $N_s$ and $N_d$ are the numbers of sources and detectors used for measurements and predictions, $z_{s,d}$ and $Q_d\psi_s$ are the measurements and the predictions for source-detector pairs (s,d) and the operator $(\;)^*$ denotes the complex conjugate of the complex vector. Measurements $z_{s,d}$ are normalized to the sum of all detection points over all illumination points divided by the total number of measurements, which provides a way that raw transmission data can be directly used as input to the reconstruction code without additional reference measurements.

Given the exemplary current estimate of forward and inverse variables $(\mu^k, \psi^k)$ the rSQP scheme makes the new iterate for both forward and inverse variables:

$$\psi^{k+1} = \psi^k + \alpha^k \Delta\psi^k$$

$$\mu^{k+1} = \mu^k + \alpha^k \Delta\mu^k \quad (6)$$

where a step length $\alpha^k$ provides a sufficient decrease in the $l_1$ merit function, and a search direction $\Delta p=(\Delta\Psi, \Delta\mu)^T$ can be obtained by solving the quadratic programming problem $$\text{minimize } \Delta p^{kT}g^k + \tfrac{1}{2}\Delta p^{kT}W^k\Delta p^k$$

$$\text{subject to } C^{kT}\Delta p^k + (A\psi - b)^k = 0 \quad (7)$$

For example, g denotes the gradient of $f$, $W^k$ denotes the full Hessian (or approximations) of the Lagrangian function $L(\psi,\mu,\lambda)=f(\psi,\mu)+\lambda^T(A\psi-b)$, and C represents the matrix of constraint gradients.

The reconstruction variables are often of different magnitudes, and this varying orders of magnitude cause difficulties in convergence. In order to alleviate this effect of different magnitudes on the reconstruction and thus to improve the behavior of an optimization method, a technique called "scaling by linear transformation of variables" can be used. The basic rule of scaling of this kind is that the reconstruction variables should be scaled to have similar magnitudes (typically, of order unity) in the region of interest, with the aim of making all scaled variables be of similar "weights" during the optimization. A generalized linear transformation of variables is used here since nonlinear transformations are possible but occasionally make the original problem more nonlinear, thus causing more difficulties. Assuming that some realistic range of values of variables during the optimization will lie in the range $a_j \le \mu_j \le b_j$, we can formulate the transformation of variables as follows:

$$\mu_j^* = \frac{2\mu_j}{b_j - a_j} - \frac{a_j + b_j}{b_j - a_j} \quad (8)$$

where $\mu^*$ are the transformed variables, $\mu$ are the original variables, and $a_j$ and $b_j$ are simple lower and upper bounds. This transformation always guarantees that $-1 \le \mu_j^* \le 1$ for all $\mu_j$, regardless of the values of $\mu_j$. This transformation given by (8) also scales the original gradient g of the Lagrangian as $$g_j^* = \frac{2g_{r,j}}{b_j - a_j}. \quad (9)$$

Besides scaling of variables, a generalized smoothing operator is used for the reconstruction on unstructured grids. In general, unstructured grids cause undesirable "grid effects" due to variation in the cell size; in other words, small cells will have smaller sensitivities and large cells will have larger sensitivities. As one remedy for this effect we use the new smoothing operator combined with rescaled gradients defined as the local scaled gradients (9) multiplied by the average cell volume, divided by the local cell volume. In this way, the rescaled gradients will be more "equal" to those obtained on uniform meshes, thus improving the quality of reconstruction. In combination to this rescaled gradient, the new smoothing operator L is defined as:

$$L(\mu_i) \propto \sum_{j \in N(i)} w_j \mu_j - w_i, \; w_i = \sum_{j \in N(i)} w_j, \quad (10)$$

where the neighborhood N(i) denotes neighbor cells j for a given cell i. The weight wj are calculated as:

$$w_j = w_{norm} \cdot \zeta_{exp}(d_{i,j}; R), \text{ for } j \in N(i) \quad (11)$$

$$\zeta_{exp}(d; R) = e^{-3(d/R)^n}, 0 < n \le 2$$

$$w_{norm} = \left(\sum_{j \in N(i)} \zeta_{exp}(i,j)\right)^{-1}$$

where $\zeta_{exp}(d_{i,j}; R)$ is the radial basis function (RBF), $w_{norm}$ is a normalized weight to ensure that each neighbor has equal influence on regularization, d is a distance from the node from its neighboring point j, and R is the correlation length used to control the influence of $\zeta_{exp}(d_{i,j}; R)$. As a result, the operator as described in (10)-(11) has the same smoothing effect regardless of the local grid density, which is desirable to eliminate "grid effects" due to variation in the cell size of unstructured grids.

Additionally, this procedure can also incorporate and/or utilize the 3D surface data obtained for each finger, described above. Using such data, a 3D finger joint mesh substantially identical to the actual geometry of each body part (e.g., finger) of interest can be generated. A typical 3D volume mesh includes approximately 30,000 tetrahedron elements. Reconstructions can be started with an initial estimate of $\mu a = 0.3$ cm$^{-1}$ and $\mu s' := (1-g) \mu s = 8$ cm$^{-1}$ for all mesh points. Additionally, after the acquisition, the imaging raw data can be further processed. In every stack of images, a fast Fourier transformation (FFT) can be performed through the stack. The FFT yields values for the amplitude, phase and the DC part. Two-dimensional DC, amplitude and phase images can also be generated for the different source positions and used as additional data at the detection and diagnosis phase.

Various sets of images 14 can be generated for display and interpretation. For example, raw absorption and scattering data reconstructed as optical property maps can be displayed. These maps can be recovered on unstructured computational grids. However, it may be preferable to further process the image data to obtain structured data.

Figure 3A:
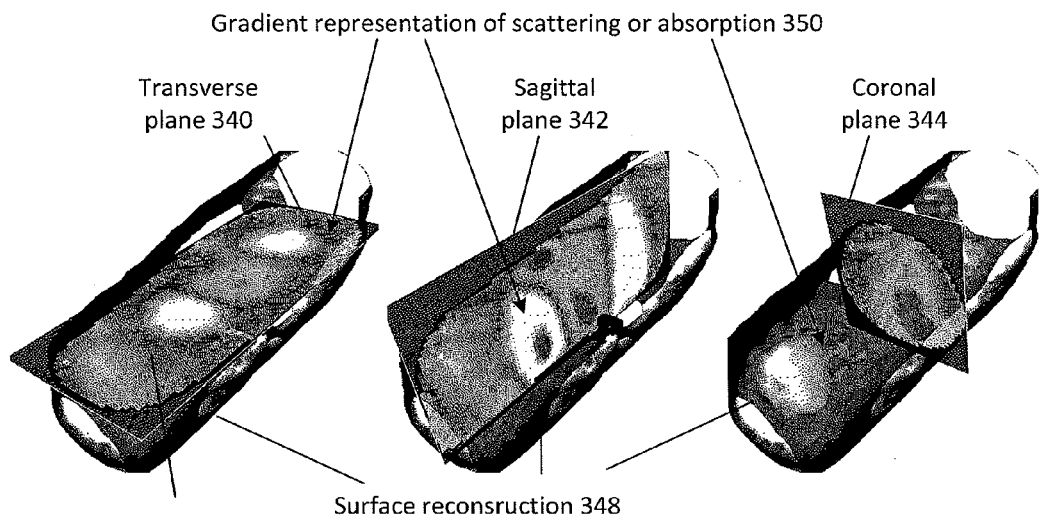
FIG. 3A shows three section planes (transverse, sagittal, and coronal) through a reconstruction of a body part according a user interface embodiment of the disclosed subject matter.
Figure 3B:
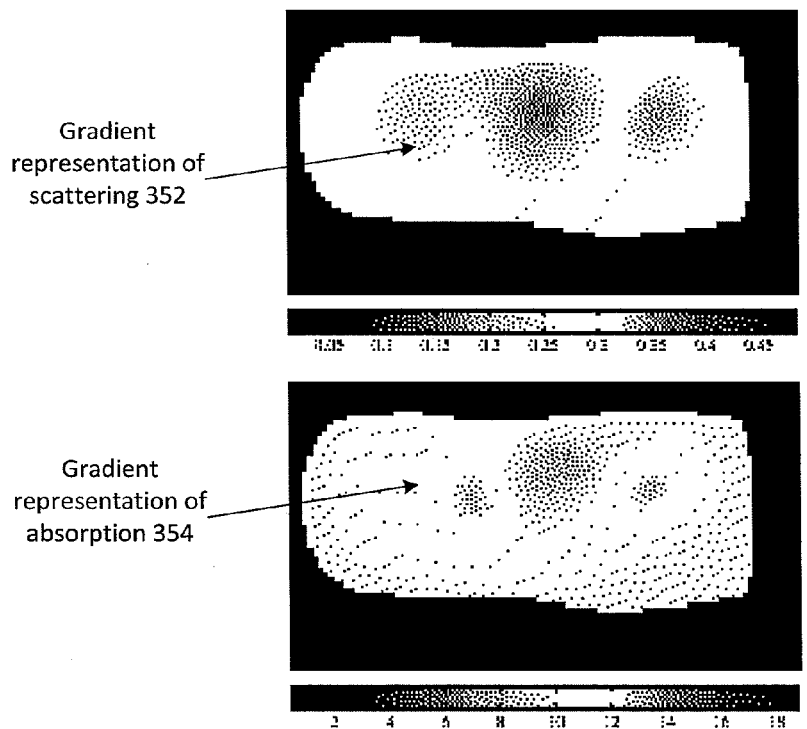
FIG. 3B shows selected section plane DOT images through a body part according a user interface embodiment of the disclosed subject matter.

Structured data can be represented as a stack of two-dimensional projections, visualized as a plurality of transverse, sagittal, or coronal cross-sectional image slices. Images can also be displayed as a stack of two-dimensional projections, visualized as a plurality of transverse, sagittal, or coronal cross-sectional image slices superposed on the 3D finger joint mesh obtained. Structured representations can also be represented by three-dimensional contour surfaces which may be rotated using a 3D mouse and displayed for image plane selection. Multiple 3D contours may be made partially transparent to allow the user to see embedded surfaces. A user may be provided the ability to select contour magnitudes to optimize such a display. In addition, the parameters of surface fits to such surface contours may be used as elements of a machine classification input vector or classifier. Such displays allow for a visualization of the different cross-sections within the 3D geometry of the finger, as shown in FIGS. 3A and 3B. FIG. 3A shows three section planes (transverse, sagittal, and coronal) through a reconstruction of a finger joint. FIG. 3B shows selected section plane DOT images through a finger joint. The transverse 340 plane, sagittal plane 342, and coronal plane 344 are shown within a broken surface reconstruction 348 of a finger in the respective views. On the plane is shown a section mapping of the reconstructed scattering or absorption coefficient. FIG. 3B shows scattering map 352 of and an absorption map 354 of a selected plane. FIGS. 3A and 3B may be used as displays of a user interface as described in respective embodiments disclosed in the present application.

A plurality of additional projection images can also be generated for each finger, as shown in Table 1 below. The first projection (projection 1) can be the raw data defined on an unstructured grid. The second projection (projection 2) is the raw reconstruction data projected onto a three-dimensional structured grid. Projections 3-11 are projections of the three-dimensional structured data onto two-dimensional domains.

TABLE 1

Definitions of projection planes

| Number | Name | Description |
| --- | --- | --- |
| 1 | UV | Entire volume (unstructured data) |
| 2 | SV | Entire volume (structured data) |
| 3 | SS | Summation of all sagittal slices |

TABLE 1-continued

Definitions of projection planes

| Number | Name | Description |
| --- | --- | --- |
| 4 | SC | Summation of all coronal slices |
| 5 | ST | Summation of all transverse slices |
| 6 | VS | Variance between sagittal slices |
| 7 | VC | Variance between coronal slices |
| 8 | VT | Variance between transverse slices |
| 9 | GS | Geometrically dominant sagittal slice |
| 10 | GC | Geometrically dominant coronal slice |
| 11 | GT | Geometrically dominant transverse slice |

Projection 3 can be obtained by summing all sagittal slices. Projections 4 and 5 can be defined as summation of coronal and transverse slices, respectively. Projection 6 can be defined as the variation between sagittal slices. This results in a sagittal slice that quantified the variation between all sagittal slices. Similarly, projection 7 and 8 quantified the variation between coronal and transverse slices, respectively.

Projections 9, 10, and 11 can be defined as the average of multiple cross-sections near the middle of the PIP joint in each of the three physiological planes. For example, projection 9 was defined as the average of all sagittal cross-sections within ±2 mm from the center of the PIP joint. Projections 9-11 are geometrically far from the tissue boundary, and are therefore less prone to contain boundary artifacts, which are well-known sources of error in optical tomographic images. Furthermore, contrast in the distribution of the optical parameters between subjects with RA and subjects without RA appeared to be at a maximum in the region around the synovium, which was expected to be easily captured by these projections.

Figure 4A:
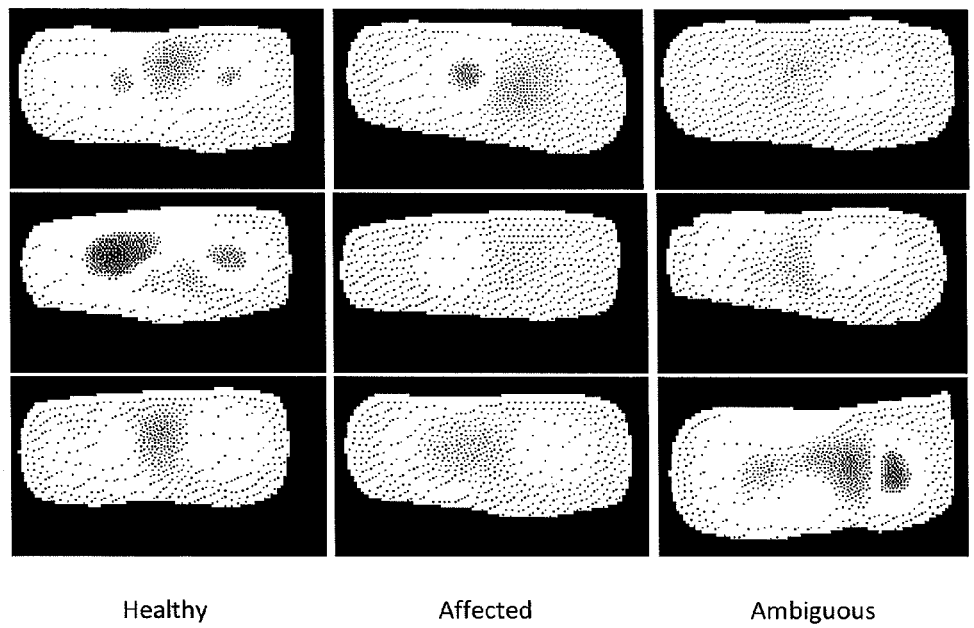
FIGS. 4A and 4B shows absorption and reduced scattering coefficient distributions in PIP joints of subjects, respectively, for healthy, affected, and ambiguous targets.
Figure 4B:
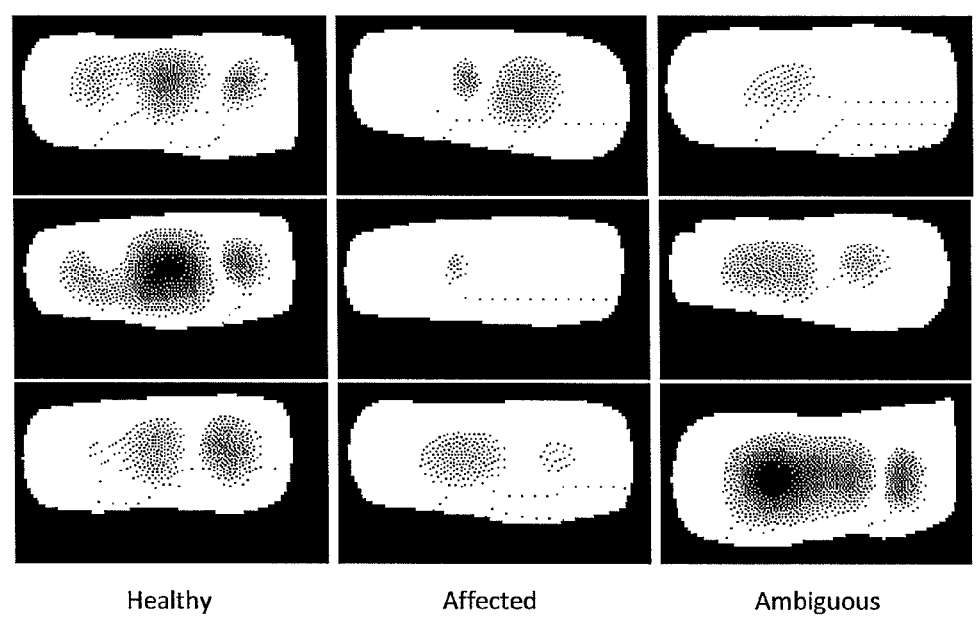

Since each reconstruction yields volumetric distributions of the absorption ($\pi_a$) and scattering ($\pi_s$) coefficients within a given finger, visualization of the reconstructed optical properties can be facilitated by displaying, for example, in a grid, the absorption and scattering coefficient distributions in the transverse, sagittal, and/or coronal cross-sectional images and projections through the finger. FIGS. 4A and 4B shows absorption and reduced scattering coefficient distributions (on transverse cross-sections) in PIP joints of subjects, respectively, for healthy (left column), affected (middle column) and ambiguous (difficult to diagnose) (right column).

Since the absorption coefficient distributions of patients with RA and patients without RA are qualitatively different (FIG. 4A, left column v. middle column), the absorption and scattering coefficient distributions in the transverse, sagittal, and/or coronal cross-sectional images through the finger carry information which is useful in diagnosing the patient, and an inspection of these images allows for a determination whether the patient does or does not have RA. In particular, these images differ in and around the region of the joint cavity, approximately located in the middle of the finger. The absorption coefficient in healthy fingers is lower than the background absorption in and around the joint cavity. In contrast, fingers affected with RA have elevated absorption coefficients in the region of the synovial cavity, making the overall absorption distribution in the cross-section more homogeneous. In many cases, however, the differences in optical properties between fingers affected with RA and healthy fingers are not easily identifiable through visual inspection (FIG. 4A right column) were obtained from healthy joints, but it is not immediately clear that these images are different from the images from affected joints.

Similar observation can be made from scattering coefficient distributions (FIG. 4B). In this case, the scattering distributions have a lower minimum inside and adjacent to the joint cavity in subjects not affected with RA. In contrast, fingers of patients with RA have a more homogeneous scattering distribution.

In breast and vascular imaging, physiological parameters, such as oxy or deoxyhemoglobin concentrations, [HbO2] and [Hb] respectively, can be reconstructed. Also possible are total blood volume [HbT] and oxygen saturation SO2, which are given by [HbT]=[HbO2]+[Hb], and SO2=[HbO2]/{[Hb]+[HbO2]}. Therefore, images represent oxy-hemoglobin concentration, deoxy-hemoglobin concentration, total blood volume or oxygen saturation can also be derived from frequency domain diffuse optical tomography and the features can include features derived from these images by parameterization of curvilinear function fits.

The distribution of the absorption and scattering coefficients vary between fingers that are affected with RA and fingers that are not affected with RA, which can make it difficult to determine which joints are affected with RA from purely visual inspections of the images. Techniques that go by various names including computer-aided algorithms, computer-aided diagnosis, computer aided classification, and computer aided detection (the acronym CAD will be used in the present application) can be used in conjunction with the visual assessment to improve the accuracy and reproducibility of disease detection and diagnosis of a disease. The detection (presence or absence) or diagnosis (normal or abnormal) of a disease can be performed using CAD based upon knowledge acquired by training on a representative sample database. The CAD performance is thus affected by the sample data in the database and the features of the data that the algorithms are trained on. Therefore, feature extraction is an important step in the image evaluation.

Figure 2B:
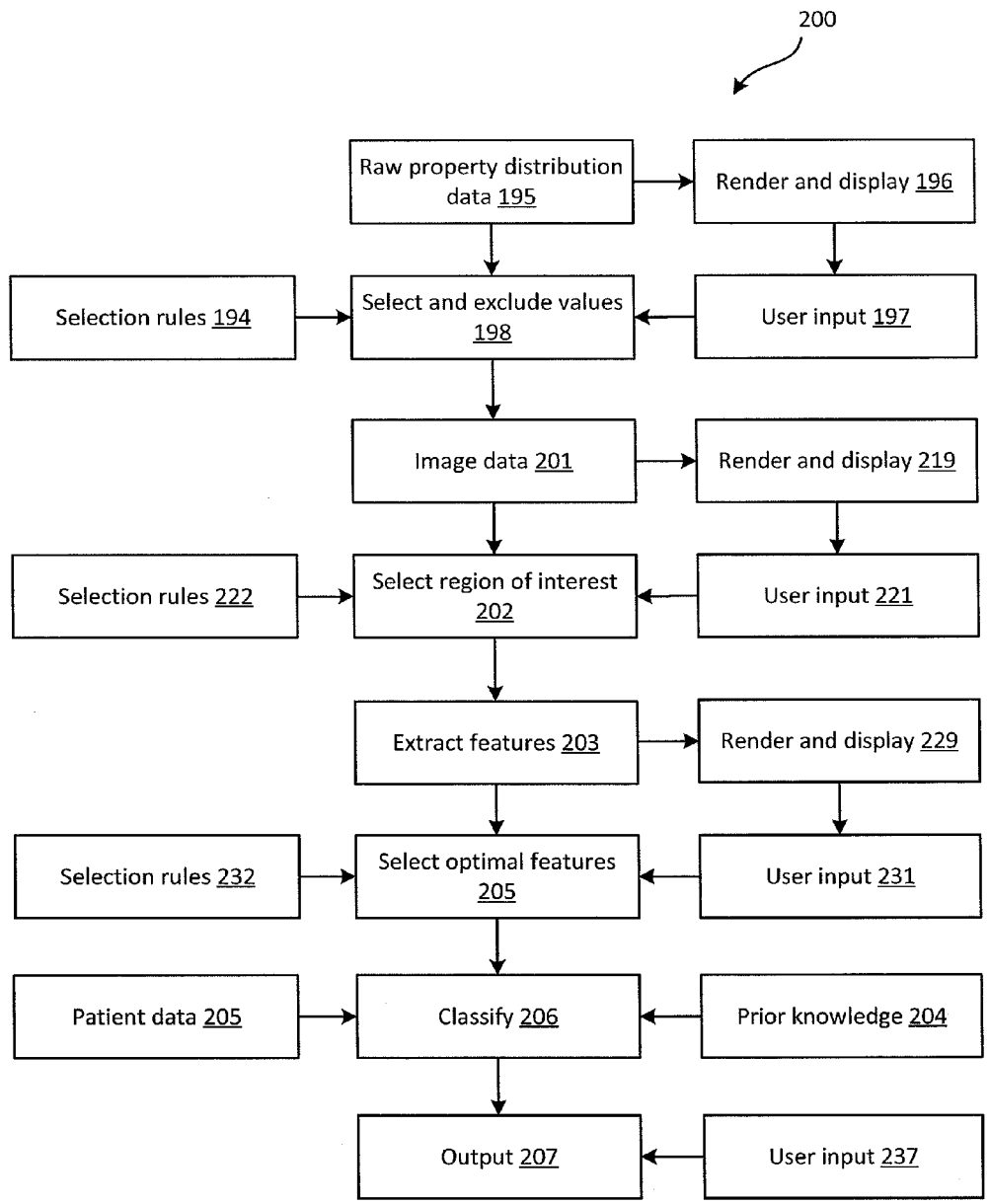
FIG. 2B illustrates a process for classifying image data according to embodiments of the disclosed subject matter.

FIG. 2B illustrates a process for a CAD system 200. Image data is acquired 201 and one or more regions of interest are selected at 202. The latter may be done by rendering and displaying 219 a representation of the anatomy (from the body part surface model) and/or structured or unstructured DOT data including scattering and absorption coefficient distributions in sections and projections and accepting input 221 by a user to select (or equivalently, unselect) regions to define a region of interest. Region selection may be done using conventional computer interaction techniques, such as indicating parts of an image using an input device such as a mouse or keyboard. A combination of the DOT data and anatomical representation may also be simultaneously displayed for this purpose.

Alternatively, or in addition, the feature selection may be done according to rules stored in a database as indicated at 222. The rules may be based on anatomical and/or physiological criteria, such as accept or use only data representing regions of anatomy lying within 2 mm of the surface of the skin. Rules may also be based on other dimensional limits such as limiting regions to those within a predefined distance from a fiducial marker. Rules may also be based on parameter thresholds, for example, screening out data by region or parameter value based on a magnitude acceptance range. Rule based selection and user selection may be combined. In one scheme, the user interface may suggest exclusion or inclusion regions of interest and allow the user to enter commands to select or deselect the rules for application or the regions defined by the rules for inclusion or exclusion. Alternatively the rules may be selected or deselected for application or bypass by user input.

In addition, or alternatively, in 202, 221, the structured or unstructured DOT data including scattering and absorption coefficient section or projection maps may be selected (again, or, equivalently, deselected). Different regions of different maps may also be selected. For example, a grid of structured or unstructured coefficient maps may be displayed and regions selected, or entire maps selected, for feature extraction in subsequent process 203.

The image data may include any and all projection images and projection data obtained as described above. The region of interest process 202 flows into a feature extraction process 203 where selected regions and/or data are processed to obtain features which are then classified in classify process 206. The classify process can have inputs such as prior knowledge 204 and patient data 205, and a final output process 207 outputs results, for example, by displaying diagnosis, classifier maps, reliability estimates, and/or other resulting data.

An optional feature selection process 205 may be included. Features may be extracted 203 and rendered and displayed at 229 for selection by user input 231. In addition, or alternatively, feature selection rules may be applied 232 to select features for inclusion in the classification process 206. Features generated for selection may be image based features such as elements of function fit such as a component of a two-dimensional multivariate Gaussian mixture model or components of a Fourier decomposition. Examples of different components or classes of features for a feature space applicable to the classification process 206 are discussed throughout the present disclosure. Representations of the features may be rendered and displayed 229 and selected 231 with the help of display highlighting using known pointing techniques using keyboard, mouse, light pen, or other suitable input techniques.

The processes 219, 221, and 222 are optional and may be omitted. Also, process 222 may be used without processes 219 and 221 or processes 219 and 221 without process 222 in respective alternative embodiments. The processes 196, 197, 198 and 194 may be included or omitted in combination with any of the above processes to form additional embodiments such that raw image data is processed according to predefined specifications as process 201. In any of the embodiments, the user interface may expose for selection, application, or modification any of the selection rules 194, 222, and 232 provided. For example, data thresholds may be displayed as numerical controls for adjustment. Examples of thresholds include allowed value ranges for parameters (e.g., absorption and scattering coefficient values) ranges and/or upper and lower limits on parameter ranges.

The selection of regions of interest may encompass fine grained selection such as stepping through many possible sections or projections interactively. FIGS. 2C and 2D show examples of methods for defining regions of interest in this manner.

In FIG. 2C, a single display is shown at different points in time at 262, 264, and 266 where selections made by a rotation control 263 have resulted in different orientations of a body part 267 (the outline or surface indicated at 267) is rotated in steps. A mapping 265 of parameters of interest such as diffusion and/or absorption coefficients may be shown. The mapping may represent a section or projection. Although shown as having defined boundaries, it will be clear that the boundaries of the mapping elements may be diffuse or may be rendered as contour maps showing discrete contours for predefined levels. At 262 the orientation shows 2 "blobs" which may provide an undesirable image from which to extract features. At 264, the display shows three blobs and at 266, the display shows 4 blobs, which may be optimal. By using the control 263, which may be any kind of control, the projection or section may be selected. Additional controls for selecting among parallel section planes along any axis may also be provided. Similar controls and displays may be used for entering exclusion regions or selection regions.

In FIG. 2D, a single display is shown at different points in time at 272, 274, and 276 where selections made by a rotation control 275 have resulted in different orientations of a body part 273 (the outline or surface indicated at 273) may be rotated progressively or in steps. A three-dimensional model 277 of parameters of interest such as diffusion and/or absorption coefficients may be shown. The mapping may represent a surface contour map, for example, or other three-dimensional representation. At 272 the orientation shows 2 a view in which multiple discrete regions are aligned in a way that their projections overlap. This may provide an undesirable section or projection image from which to extract features. At 274, the display shows a changed orientation. By using the control 275, which may be any kind of control, the orientation of the model 277 may be changed allowing the user to visualize and thereby hunt for section or projection having desired characteristics. Additional controls for selecting among parallel section planes along any axis may also be provided. Similar controls and displays may be used for entering exclusion regions or selection regions.

As discussed above, the user input processes 197, 221, and 231 allow users to choose among various input settings in order to manipulate data acquisition, projection image generation, feature extraction, classification algorithms, and display, based on different classes of user. The factors may include user experience, and preference. For example, if the user is a technician, for example, the processing system 9 will run based on a predetermined set of default settings that will automatically apply a pre-set image reconstruction algorithm, projection image generation, projection image display, feature extraction algorithm, classification algorithm, and result display. On the other hand, if the user is experienced in reviewing, identifying and/or diagnosing a particular condition, he/she has the option to change any of the processing and display parameters listed above. For example, the user can change the number of projection and reconstruction images to be used and/or displayed, can choose the specific feature extraction algorithm, can specify the features to be extracted, can choose the classification algorithm used to classify the feature groups, can use additional classifiers, and can choose a particular image and/or marker to be displayed for diagnosis and interpretation. It can also fine-tune any of the above-listed parameters, images, classifiers. In addition, as indicated at 237 in FIG. 2B and as discussed elsewhere, the forms of output may also be varied according to user taste or class.

Referring again to FIG. 2A, once the image reconstruction is completed, the acquired images can be further processed for display as color gradient maps, contour maps, 3D surface projections, etc. According to a user interface embodiment, images 14 may be displayed on a user interface display 13 to permit one or more to be selected for further processing, manipulation, and/or display. The process of selection may be automatic or manual or a mixture of the two. The options account for the fact that systems may be provided for use by different classes of users. For all classes of users, the system may provide a "default" setting that can be applied, which includes a pre-set image reconstruction algorithm, projection image generation, projection image display, feature extraction algorithm, classification algorithm, and image display. For a specialist may have controls available for a variety of different parameters that he/she can utilize to display different images and/or to accurately interpret the images. For example, a drugstore kiosk version may be completely automated and provide a screening function. For example, such a kiosk may provide an aperture to receive a finger and provide a completely automated DOT scanning sequence which results in a clear output such as a diagnosis, severity metric, and reliability score. At the other end of the spectrum are sophisticated users who specialize in the most effective use of OT for detecting disease or other anatomical and/or physiological indicators. For such users, the system may present many controls and intermediate levels of output providing parameter selection control, scan plane selection, deletion of features classified automatically, and selection of machine classifier input vectors and vector elements. For example, the experienced user may be provided the ability to change the number of projection and reconstruction images to be used and/or displayed, choose the specific feature extraction algorithm, specify the features to be extracted, choose the classification algorithm used to classify the feature groups, the use additional features and classifiers, choose a particular image and/or marker to be displayed for diagnosis and interpretation.

Note the above discussion blurs the distinction between features and images, for example, since the 3D model or 2D contour map requires defining surfaces. It will be understood that in the process diagram of FIG. 2B, primitive features may be encompassed by what is identified in the drawing as images. FIGS. 2C and 2D also illustrate an example of an automatic section/projection selection method. Selection rules 222 may specify that the number of "blobs" should be minimized. Again, since the maps are diffuse and smooth, there are not expected to be discrete boundaries of the peaks and valleys of the coefficient maps so the term blob is used figuratively. Various means for accomplishing this may be devised, for example, maximizing the spacing between peaks, defining contours for purpose of defining discrete blobs and counting, and assigning contours to standard deviations of components of Gaussian fits to the raw data and then counting.

Features extracted in process 203 may be divided into two categories: (1) volumetric features and (2) projection dependent features. Volumetric features may be divided into two categories: (a) basic features and (b) spectral features. Projection dependent features are features that can be extracted from the projections obtained by projecting reconstructed optical properties into various two-dimensional spaces, as shown in detail above.

The basic volumetric features can be extracted from all 11 projections described above. For example, features can be obtained by arranging the optical parameter distributions into vectors of ascending value. Each reconstructed property, x, can be expressed as $x=[x_1, x_2, x_3, x_N]$, where the computational domain has N discrete (mesh) points and $x_i$ is the optical property at the $i^{th}$ node.

The average maximum can be defined as the average of the nth largest coefficients across the entire reconstructed volume, while the average minimum can be defined as the average of the nth smallest coefficients across the volume (n=10). The mean, mode, median, and variance can be defined as the variance between non-extreme elements of x. That is, the nth largest and nth smallest coefficients can be discarded. A fourth feature can be defined as the ratio between maximum and minimum. The volumetric features so obtained are shown in Table 2 below.

TABLE 2

Definition of volumetric features

| Feature Number | Description |
|---|---|
| 1 | Maximum |
| 2 | Minimum |
| 3 | Mean |
| 4 | Mode |
| 5 | Median |
| 6 | Variance |
| 7 | Ratio of maximum/minimum |

Additional 15 features can be extracted from projections 3-11 by parameterizing the distribution of the optical coefficients with a two-dimensional multivariate Gaussian mixture model.

The mixture model can be fitted by finding estimates for amplitude A, covariance matrix $\Sigma$ and mean of Gaussian function, G, $$G(x) = A_0 \exp[-\frac{1}{2}(x-x_0)^T \Sigma^{-1}(x-x_0)] \quad (8)$$

so that the least squares error, $\epsilon = \Sigma(I(x_i) - G(x_i))^2$, can be minimized with respect to the original data, I. The original data can be smoothly distributed as represented by FIGS. 5A and 5B which show the original scattering distribution. The parameterized scattering data are shown in FIGS. 5C and 5D. FIGS. 5A and 5C show data for a healthy subject and FIGS. 5B and 5D show data for a subject with RA. As may be seen, the smoothness of the DOT data allows the GMM to provide a close approximation with few components. The model data allows for more advanced statistical analysis because the entire cross sectional image can be described by a few Gaussian parameters.

Features describing the parameterization of the concave and convex regions can be extracted, including the number of concave/convex Gaussian and the absolute error between the mixture model and the original data. In addition, parameters that describe the dominant concave and convex regions can also be extracted. This can include local amplitudes, diagonal elements of local Gaussian covariance, determinants of the covariance matrices, the absolute value of the covariance matrix cross correlation, and the diagonal elements of the covariance matrix divided by the amplitude of its Gaussian function, as shown in Table 3 below.

TABLE 3

Definition of parameterization features

| Feature Number | Description |
|---|---|
| 8 | Number of convex Gaussians |
| 9 | Number of concave Gaussians |
| 10 | Amplitude of dominant convex region |
| 11 | Amplitude of dominant concave |
| 12 | Variance in x-direction of dominant convex |
| 13 | Variance in x-direction of dominant concave |
| 14 | Variance in y-direction of dominant convex |
| 15 | Variance in y-direction of dominant concave |
| 16 | Determinant of dominant convex |
| 17 | Determinant of dominant concave |
| 18 | Absolute value of cross-correlation for dominant Gaussian convex |
| 19 | Absolute value of cross-correlation for dominant Gaussian concave |
| 20 | Variance in x-direction of dominant valley divided by corresponding value for dominant concave |

TABLE 3-continued

Definition of parameterization features

| Feature Number | Description |
|---|---|
| 21 | Variance in y-direction of dominant valley divided by corresponding value for dominant concave |
| 22 | Absolute error between original ROI and model Gaussians |

Combined, these features provide information on the distribution of the optical properties inside the finger. Many different basic and parameterization features can be extracted from each finger's $\mu_a$ and $\mu'_a$ distributions.

A shorthand notation can be used to refer to extracted features throughout the specification. For example, the convention can be "Feature Number: Projection Name: Optical Parameter." For example, the number of concave Gaussians that can model the geometrically dominant sagittal slice in the scattering distribution images could be referred to in shorthand notation as F8:GS:s. The indices "a" and "s" denote absorption or scattering distribution derived features, respectively.

Additional features may be extracted from projection 2 and projections 3-11 using the three- and two-dimensional discrete fast Fourier transform (DFFT), respectively. Projection 2 can be analyzed with a three-dimensional DFFT. The coefficients belonging to the first 5 frequencies can be retained, resulting in a total of 125 coefficients. These 125 features can be reduced to 63 because 62 of them are the complex conjugates of 62 of the other features. Projections 3-11 can be analyzed with the two-dimensional DFFT to obtain the coefficients of the first 5 leading frequencies. This can generate additional 13 coefficients.

Prior to feature extraction, one or more regions of interest (ROI) in a projection, section, or 3D (three-dimensional) region of interest (ROI) may be determined for each body part from which to extract the feature by feature extraction processor 202. The region of interest (ROI) can be defined in several ways. For example, the entire image may be initially processed for feature extraction by feature extraction processor 202. Alternatively, a part of the image could be selected as the region of interest. The segmentation of the region of interest can be performed manually or automatically. For example, if the segmentation is done manually, the user (medical personnel) can delineate a region of interest on an image displayed on the display device using a mouse, pointer, etc. Otherwise, segmentation can be performed automatically by implementing a segmentation algorithm, which can delineate a region of interest based on prior knowledge about the imaged body part. A combination of the manual and automatic delineation of the region of interest can also be implemented.

Figure 6:
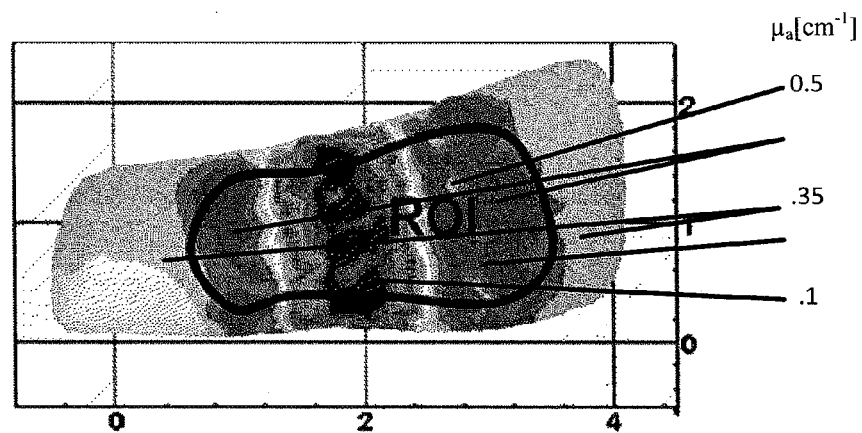
FIG. 6 shows a two-dimensional cross-section through a three-dimensional reconstruction of the distribution of the absorption coefficients in a finger joint.

FIG. 6 shows a two-dimensional cross-section through a three-dimensional reconstruction of the distribution of the absorption coefficients in a finger joint. Also shown is a selected region of interest (ROI), for which various optical parameters were determined. The ROI was limited to regions at least 3 mm away from boundaries and within the lateral extent of the source and detector placement. Typically only mesh points that are at least about 2 mm away from a tissue boundary eliminate reconstruction artifacts that are at times visible near tissue boundaries. Further, mesh points that are within the lateral extent of the light illumination points are typically included in the ROI. Exemplary measurements within this range can provide useful information for the reconstruction code.

From each 3D ROI, the various feature parameters as described above can be extracted, all or some of which can be subsequently used for computer-aided diagnostics.

In order to sort through the candidate features and select only the useful features and remove the features that provide no information or redundant information, a plurality of feature selection algorithms, such as the Kruskall-Wallis, the Dunn, and the Receiver Operator Characteristic (ROC) analysis tests, can be employed to extract the optimal features.

These algorithms analyze the plurality of features extracted from the plurality of reconstructed and projection images, and evaluate each feature in terms of its ability to separate different classification groups (affected with RA or not affected with RA, for example), namely, they rank the features based on their ability to differentiate between different groups. This optimal feature selection is also used to reduce the computation time which might be too long if the number of features to compute is too large. The output of the optimal feature extraction process is a reduced set of features including optimal features which are the best classifiers.

For example, the utility of each feature for classification can be gauged by statistical analysis on the (null) hypothesis that there are no statistically significant differences between the diagnosis groups and the control group. The following three steps can be taken in analyzing the statistical significance of each feature.

In step 1, through goodness of fit analysis it can be determined whether there is only a small likelihood that the extracted features were drawn from a normally distributed population. In step 2, the non-parametric (distribution-free) Kruskal-Wallis test can be used to determine if at least one of the groups exhibits statistically significant differences from the other groups. The observed differences between the groups can be determined to be statistically significant if the H-statistic is larger than the corresponding critical value from a distribution table with $v=T-1$ degrees of freedom, where T is the number of distinct groups.

In step 3, group-to-group comparison using Dunn's test can be performed to determine which groups are significantly different from each other. This test allows direct comparison of two groups that do not have the same size.

Receiver operator characteristic (ROC) analysis can be used to find the features that are individually the best classifiers. In ROC analysis, the threshold value that best separates two groups (i.e. one group with the disease and one without the disease) can be determined. The best threshold is the feature value x that maximizes the Youden index (Y), which is defined as $Y=Se+Sp-1$, where $Se=TP/(TP+FP)$ and $Sp=TN/(TN+FN)$.

All patients with RA can be grouped into a single group and compared against the second, healthy group. A feature that separates the affected (i.e. PIP joints of subjects with RA) from the healthy would yield $Y=1$, while a feature that fails to separate the two groups would yield $Y=0$. Thus, ROC analysis of each feature can be used to evaluate the classification strength of each feature.

Determination of the optimal set of features can be done by developing an evolution strategy algorithm. Generally referred to as $(1, \lambda)$ single parent evolution strategy (ES), this evolution strategy is an optimization technique based on ideas of adaptation and evolution. It can use two steps: (1) mutation and (2) selection as its search operator. In the mutation step, $\lambda$ mutants can be generated to compete with their parents. In the selection step, new parents can be selected from the set of previous generation parents and their $\lambda$ mutants. The selection can be made based on the fitness ranking, not on the actual fitness values. The operator can be applied in a loop. An iteration of the loop is called a generation. The sequence of generations can be continued until a termination criterion is met.

This $(1, \lambda)$ evolution strategy can be used to find the feature combinations with highest Youden (Y) indices. The process can be summarized as follows:
1. An initial feature combination is chosen as the first generation parents.
2. All possible mutants are generated by adding, dropping, or replacing one feature from the parent combination.
3. Of all the mutants and their parent, the combination with the highest Youden index becomes the parent in next generation.
4. Repeat this process until the Youden index cannot be improved.

This problem can be cast as an optimization problem, where the objective function, can be defined as the as the average Youden index over N iterations of the kth set of feature combinations in the $\lambda$ generation.

$$\phi_{\lambda+1} \to \max_{\lambda,k} \phi_\lambda^k = \frac{1}{N} \sum_i^N (Se_i^k + Sp_i^k - 1) \tag{9}$$

Figure 7A:
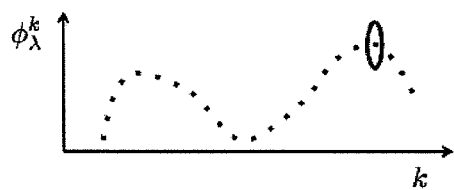
FIGS. 7A and 7B illustrate an optimization technique with 7A showing a sample within-generation value of an object function for all possible feature combinations (mutants) and FIG. 7B showing a sample evolution of an objective function over multiple generations.
Figure 7B:
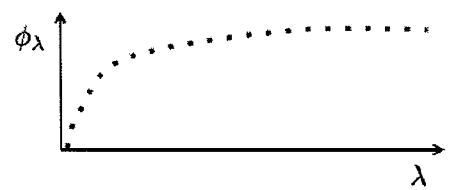

The set of features that maximizes the objective function in the k generation becomes the parents of the generation (FIG. 7A). This process guarantees that the sensitivities and specificities will increase with every new generation and that the solution will converge to a near optimal feature combination (a local maximum) that maximizes the objective function (FIG. 7B).

Once the features are computed as described above in the feature selection algorithm, and an optimal set of features is produced, a pre-trained classification algorithm can be used to classify in 206 the regions of interest into RA affected or not affected, healthy or diseased, or any other classifications that can be employed for the particular medical condition involved. The set of optimal features obtained in 203 can be used as inputs to the classification algorithm. Different classification methods can be used, such as, but not limited to, Bayesian classifiers, neural networks, rule-based methods, fuzzy logic, clustering techniques, and similarity measures. For example, the nearest neighbors method (KNN), discriminate analysis (DA) (linear and quadratic), self-organizing maps (SOM), and support vector machines (SVM) can be used as classification algorithms. Additionally, other classifying features, such as, but not limited to, prior knowledge from training 204, raw image acquisition data, higher order Gaussians and paraboloids, combinations of different modulation frequencies, spatial distribution models, patient demographic data, wavelet coefficients, or any other classifying features that can be computed, measured, or which just exist, and which are capable of yielding optimum cross-validation classification accuracy, can be used, such as, but not limited to patient data 205.

Once the classification algorithm labels the feature groups, it outputs a result which classifies the data, its location, or any other characteristic or feature that can help the reviewer identify a condition or a disease, etc. The result can be displayed in step 207 of FIG. 2B in various ways for the reviewer. For example, the results can be shown as a point on a self-organizing map (SOM), SVM map, KNN map. Alternatively, or selectively, the point may be shown with other representative points that are clearly associated with one class or the other or those used to train the classifier. The display may be a 2D, 3D, or higher dimensional map. The dimension of the map depends in the number of features involved. For example, if 8 different features are used in the final classification, the resulting points are located in an 8-dimensional space. See also the discussion of FIGS. 15A and 15B, below.

Figure 8A:
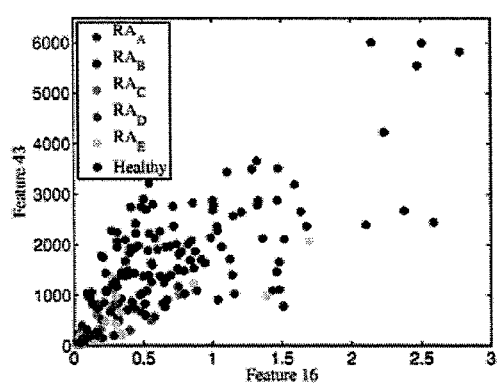
FIGS. 8A and 8B show the distribution of group-specific two-dimensional features.
Figure 8B:
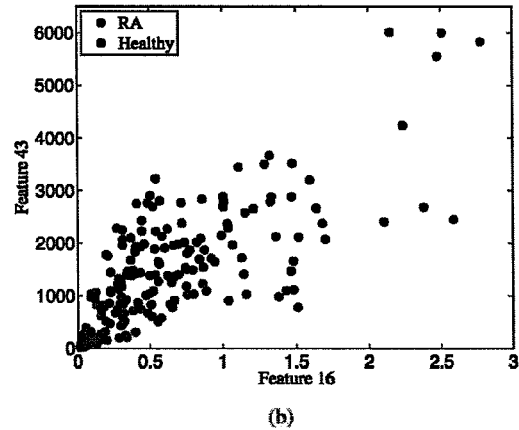
Figures 8C, 8D:
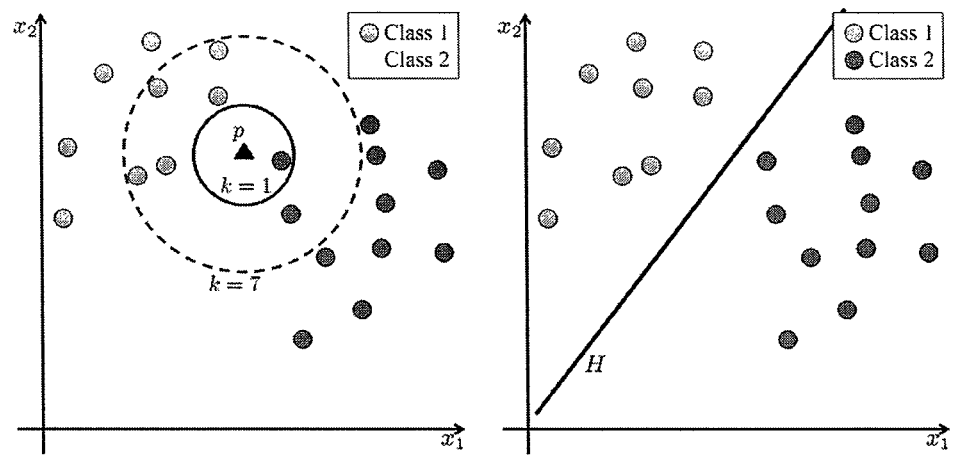
FIGS. 8C through 8F show examples of result presentation output formats for presenting classification results to a user.

FIGS. 8A and 8B show the distribution of group-specific two-dimensional features. In FIG. 8A, the six distinct diagnosis groups (A, B, C, D, E, and H) have been identified, while in FIG. 8B the five cohorts that have been diagnosed with RA have been grouped into one single group.

Figures 8E, 8F:
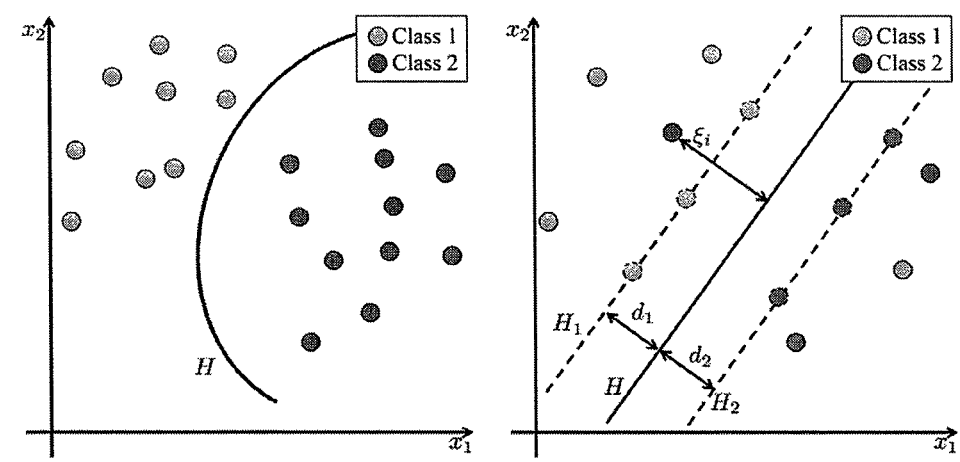
Figure 10A:
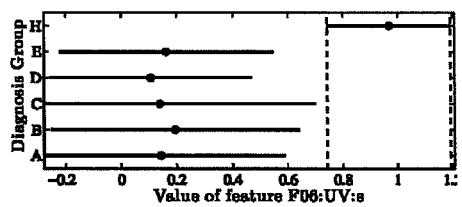
FIG. 10(a) through FIG. 10(d) present plots of group means and standard error bars to highlight observed differences between various data groups for four particular classifier features.
Figure 10B:
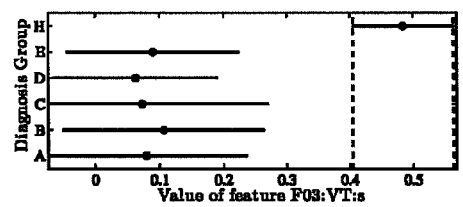
Figure 10C:
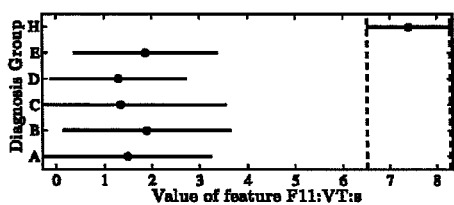
Figure 10D:
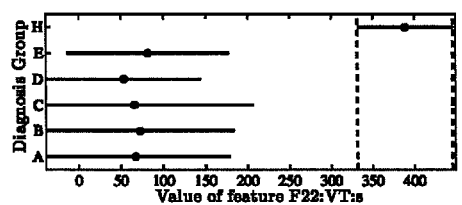

FIGS. 8C through 8F show examples of discriminant decision boundaries and sample data which may be used for presenting classification results to a user. Shown are a KNN boundary (FIG. 8C), linear boundary (FIG. 8D), and quadratic boundary (FIG. 8E). In the case of KNN, examples of k=1 and k=7 rule is shown. FIG. 8F shows an example of an SVM decision boundary for a non-linearly separable 2-class problem.

A method for extracting image features from optical tomographic images that can be used for subsequent image classification, as described above, was tested on a set of optical tomographic images of PIP joints obtained from a clinical study. The general framework included extracting three types of features from volumetric absorption and scattering images. First, basic statistical features were computed from the images. Next, a Gaussian mixture model (GMM) was fit to each image and the model parameters were extracted as features. Then, coefficients from the Fourier transform of the images were extracted as additional features. A total of 784 features were extracted from the reconstructed optical parameters of each finger joint.

The Kruskal-Wallis test and Dunn's test were used to establish that they were statistically significant differences between the features extracted from PIP joints of subjects with RA and features extracted from PIP joints of control subjects without RA. In particular, a subgroup of the subjects with RA who did not exhibit detectable signs of RA on MRI and US scans were shown to have optical properties not different from the group of subjects that did show signs of RA on the MRI and US scans. This is an important finding because it shows that OT can detect the presence of RA even when US and MRI scans cannot detect effusion, synovitis, or erosion in the joint cavity.

Finally, ROC curve analysis was used to quantify the classification strength of each extracted feature. A total of 17 features were found that yielded a Youden index greater than 0.8, where 16 of these features were derived from the scattering coefficient images. While this framework was tested on OT images of PIP joints, its flexibility allows it to be applied to other types of OT images, including breast images.

Images reconstructed from 600 MHz data allowed classification with 91% sensitivity and 86% specificity. In addition, it was shows that classification with features derived from scattering coefficient images allowed more accurate classification of PIP joints. Classification of absorption coefficient images reconstructed from 600 MHz data was classified with up to 83% sensitivity and 83% specificity, while scattering coefficient images allowed classification with up to 91% sensitivity and 86% specificity.

The general approach to image classification has been a two-step method: (1) features are extracted from OT images of PIP joints and (2) these features are subsequently used to classify each PIP joint as affected or not affected by RA. Then, classification with all possible combinations of features was performed (i.e. classification was performed in two-, three-, and four-dimensional feature space). 784 features were extracted from the OT images of PIP joints and applied 5 different classification schemes that resulted in a very broad analysis of the data.

A total of 56 volunteers were enrolled, including 36 subjects with various stages of RA and 20 healthy control subjects. Each volunteer was subject to clinical evaluation by a rheumatologist, which led to a positive or negative diagnosis for RA according to the guidelines set forth by the American College of Rheumatologist (ACR).

Each subject was evaluated for RA using the criteria outlined by the American College of Rheumatology (ACR). The clinically dominant hand of each subject was imaged with ultrasound (US) and low-field magnetic resonance imaging (MRI).

The US and MRI images were evaluated by a radiologist and a rheumatologist in a blinded-review. The images were scanned for the presence of effusion, synovitis, and erosion in PIP joints II-IV. Each reviewer classified each subject into one of five sub-groups on the basis these findings (Table 4). A third reviewer (a rheumatologist) was used as a tiebreaker in cases where the initial reviewers had differing opinions. Finally, the subgroup of patients without signs of joint effusion, synovitis, and erosion were divided into two subgroups: (1) subjects with RA and (2) subjects without RA.

TABLE 4

Diagnostic table based on clinical evaluation and radiological imaging (ultrasound and MRI)

| Group | Effusion | Synovitis | Erosion | RA |
|---|---|---|---|---|
| A | No | No | No | Yes |
| B | Yes | No | No | Yes |
| C | No | No | Yes | Yes |
| D | No | Yes | No | Yes |
| E | Yes | Yes | Yes | Yes |
| H | No | No | No | No |

Imaging with a FD-DOT sagittal laser scanner of PIP joints II-IV was performed on the clinically dominant hand of subjects with RA and on both hands of the control cohort. A frequency-modulated laser beam (670 nm, 8 mW, 1.0 mm diameter) scanned the back of a finger, stopping at 11 discrete locations along a sagittal plane to allow for data acquisition. Trans-illumination was recorded from each source position at the front of the finger with an intensified CCD camera. The three-dimensional geometry of the scanned finger was obtained with a separate laser-scanning unit (650 nm, 5 mW, 0.2 mm line width). Imaging was performed at 0, 300, and 600 MHz. In total, 228 fingers were imaged. The data from 3 subjects with RA was discarded due to errors in data acquisition. Trans-illumination measurements were used to reconstruct the tissue absorption and scattering coefficient distributions. Optical parameters were reconstructed using a PDE-constrained optimization algorithm, where the equation of radiative transfer equation (ERT) is used to model propagation of near infrared (NIR) light in tissue.

Each FDOT reconstruction yields volumetric distributions of the absorption ( ) and scattering ( ) coefficients within a given finger. Visualization of the reconstructed optical properties is facilitated by inspecting a transverse cross-section through the finger.

Feature extraction was compartmentalized into two categories: (1) volumetric features and (2) projection dependent features. Volumetric features were divided into two categories: (a) basic features and (b) spectral features. The second category refers to the process of projecting the reconstructed optical properties into various two-dimensional spaces and extracting features from these projections. Eleven distinct projections were defined for each finger as described above.

The basic volumetric features were extracted from all 11 projections of the data. They were obtained by arranging the optical parameter distributions into vectors of ascending value. Each reconstructed property, x, can be expressed as x=[, , , Ӥ ,], where the computational domain has N discrete (mesh) points and is the optical property at the node.

The average maximum was defined as the average of the nth largest coefficients across the entire reconstructed volume, while the average minimum was defined as the average of the nth smallest coefficients across the volume (n=10). The mean, mode, median, and variance were defined as the variance between non-extreme elements of x. That is, the nth largest and nth smallest coefficients were discarded. A fourth feature is defined as the ratio between maximum and minimum.

Additional 15 features were extracted from projection 3-11 by parameterizing the distribution of the optical coefficients with a two-dimensional multivariate Gaussian mixture model as described above. Parameterization with a Gaussian mixture model was chosen because the reconstructed distributions of the optical properties were expected to be smooth; this expectation is derived from the fact that OT reconstructions allow only smooth solution.

The mixture model was fitted by finding estimates for amplitude, covariance matrix $\Sigma$ and mean of Gaussian function, G, $$G(x)=A_0\exp[-\tfrac{1}{2}(x-x_0)^T\Sigma^{-1}(x-x_0)] \qquad (10)$$

so that the least squares error, $\epsilon=\Sigma(I(x_i)-G(x_i))^2$, was minimized with respect to the original data, I. The original data was smoothly distributed (FIGS. 5A and 5B). The mixture models proved to result in close approximations (FIGS. 5C and 5D) to the original data. The model data however, allows for more advanced statistical analysis because the entire cross sectional image is described by only a few Gaussian parameters.

Features that described the parameterization of the concave and convex regions were extracted, including the number of concave/convex Gaussian and the absolute error between the mixture model and the original data. In addition, parameters that described the dominant concave and convex regions were extracted; including local amplitudes, diagonal elements of local Gaussian covariance, determinant of the covariance matrices, the absolute value of the covariance matrix cross correlation, and the diagonal elements of the covariance matrix divided by the amplitude of its Gaussian function.

Combined, these features provide information on the distribution of the optical properties inside a finger. In total, 70 basic and 135 parameterization features are extracted from each fingers and distributions (leading to 410 features).

Additional features were extracted from projection 2 and projections 3-11 using the three- and two-dimensional discrete fast Fourier transform (DFFT), respectively. Projection 2 was analyzed with a three-dimensional DFFT. The coefficients belonging to the first 5 frequencies were retained, resulting in a total of 125 coefficients. Since only the absolute values of the coefficients were stored, these 125 features were reduced to 63 because 62 of them were the complex conjugate of 62 of the other features. Projections 3-11 were analyzed with the two-dimensional DFFT. Only the coefficients of the first 5 leading frequencies were stored, which required storing 13 of 25 coefficients.

The utility of each feature for classification was gauged by statistical analysis on the (null) hypothesis that there were no statistically significant differences between the 5 diagnosis groups (A-E) and the control group (H). The following three steps were taken in analyzing the statistical significance of each feature.

In step 1, through goodness of fit analysis it was determined that there was only a small likelihood that the extracted features were drawn from a normally distributed population. In step 2, the non-parametric (distribution-free) Kruskal-Wallis test was used to determine if at least one of the six groups exhibited statistically significant differences from the other groups. The observed differences between the groups were statistically significant if the H-statistic was larger than the corresponding critical value from a distribution table with v=T-1 degrees of freedom, where T was the number of distinct groups.

In step 3, group-to-group comparison using Dunn's test was performed to determine which groups were significantly different from each other. This test was chosen because it allowed direct comparison of two groups that did not have the same size. Dunn's test was used to compare all possible 2 subgroup combinations (i.e. A vs. B, A vs. C, A vs. D, etc.).

Receiver operator characteristic (ROC) analysis was used to find the features that were individually the best classifiers. In ROC analysis, the threshold value that best separated the two groups was determined (i.e. one group with the disease and one without the disease). The best threshold was the feature value x that maximized the Youden index (Y), which was defined as Y=Se+Sp-1, where Se=TP/(TP+FP) and Sp=TN/(TN+FIV).

All patients with RA (groups A, B, C, D, and E) were grouped into a single group and compared against the healthy group (H). A feature that perfectly separated the affected (i.e. PIP joints of subjects with RA) from the healthy would yield Y=1, while a feature that completely failed to separate the two classes would yield Y=0. Thus, ROC analysis of each feature was used to evaluate the classification strength of each feature.

Sample results from data projection, parameterization, and spectral analysis are presented in FIGS. 9A, 9B, and 9C. The top image in each of FIGS. 9A, 9B, and 9C correspond to the geometrically dominant cross-sectional slices of the scattering coefficient in the sagittal, transverse and coronal planes (projections 9, 10, and 11). The middle image in each of FIGS. 9A, 9B, and 9C was reconstructed from only the first five Fourier frequencies. They are representative of the level of detail captured by the Fourier coefficients that were extracted as features. The first five frequencies captured the general distribution of the scattering coefficient. Preserving only the first five frequencies minimizes the contribution from pixels near the boundary, because values near boundary are more prone to numerical error and noise. Images the bottom image of each of FIGS. 9A, 9B, and 9C represents the parameterization of the original data with a two-dimensional Gaussian mixture model. Parameterization of the data completely removed the contribution from the boundary, leaving only the major structures, which were all in the interior. In general, the parameterization is a good approximation to the original data. Similar results were found for the absorption coefficient distribution.

Results from the Kruskal-Wallis comparison of groups A-H using basic features and features extracted from Gaussian parameterization are summarized in Table 5 for $\mu_s$. The number of distinct groups (k) was 6, thus, H-statistics greater than 11.07, 15.09, and 20.52 were necessary to establish statistical significance in observed difference at the 0.05, 0.01, and 0.001 confidence level. The H-statistic was less than 11.07 for 129 features and greater than 20.52 for 242 features. H-statistic values that were above 100.0 are highlighted in bold.

TABLE 5

H-statistics from Kruskal-Wallis ANOVA test results using $\mu_a'$ derived features

| Feature | UV | SV | SS | SC | ST | VS | VC | VT | GS | GC | GT |
|---|---|---|---|---|---|---|---|---|---|---|---|
| 1 | 124.28 | 123.44 | 61.31 | 95.93 | 54.27 | 132.79 | 141.89 | 139.66 | 115.54 | 75.23 | 122.59 |
| 2 | 138.99 | 134.99 | 38.27 | 45.52 | 63.66 | 1.81 | 3.27 | 1.15 | 13.58 | 51.52 | 120.35 |
| 3 | 108.41 | 119.46 | 23.16 | 22.44 | 11.88 | 146.12 | 142.30 | 146.71 | 116.29 | 44.58 | 135.58 |
| 4 | 150.66 | 97.40 | 23.05 | 22.44 | 11.88 | 125.93 | 123.46 | 103.84 | 119.35 | 119.46 | 119.46 |
| 5 | 0.00 | 130.41 | 23.16 | 22.44 | 11.88 | 1.81 | 3.27 | 1.15 | 119.46 | 119.46 | 119.46 |
| 6 | 0.00 | 142.95 | 135.63 | 132.25 | 133.45 | 138.87 | 140.62 | 141.12 | 129.09 | 115.83 | 139.07 |
| 7 | 144.98 | 144.69 | 112.84 | 133.91 | 141.95 | 63.30 | 77.35 | 77.08 | 99.73 | 104.98 | 135.07 |
| 8 | — | — | 26.36 | 17.55 | 6.38 | 0.00 | 0.00 | 0.00 | 10.21 | 10.35 | 13.39 |
| 9 | — | — | 17.83 | 54.86 | 36.68 | 8.88 | 0.00 | 3.13 | 35.64 | 28.51 | 11.88 |
| 10 | — | — | 77.32 | 109.72 | 90.55 | 0.00 | 0.00 | 0.00 | 62.19 | 129.37 | 72.81 |
| 11 | — | — | 63.35 | 73.97 | 99.63 | 127.83 | 136.57 | 140.36 | 111.98 | 111.06 | 58.44 |
| 12 | — | — | 6.79 | 26.26 | 18.16 | 0.00 | 0.00 | 0.00 | 9.36 | 78.33 | 14.63 |
| 13 | — | — | 9.85 | 4.51 | 9.53 | 6.21 | 4.83 | 7.81 | 19.21 | 9.37 | 9.66 |
| 14 | — | — | 18.08 | 21.60 | 30.69 | 0.00 | 0.00 | 0.00 | 15.77 | 58.25 | 11.15 |
| 15 | — | — | 21.33 | 9.91 | 43.04 | 7.42 | 14.99 | 12.82 | 10.06 | 5.43 | 3.86 |
| 16 | — | — | 10.49 | 24.77 | 19.74 | 0.00 | 0.00 | 0.00 | 21.60 | 81.86 | 13.69 |
| 17 | — | — | 28.53 | 11.03 | 40.91 | 6.74 | 4.77 | 1.32 | 15.54 | 3.77 | 8.18 |
| 18 | — | — | 24.60 | 20.37 | 22.48 | 0.00 | 0.00 | 0.00 | 14.45 | 16.90 | 5.11 |
| 19 | — | — | 14.42 | 21.25 | 25.37 | 6.12 | 26.57 | 3.92 | 6.94 | 6.46 | 4.96 |
| 20 | — | — | 9.18 | 22.97 | 12.64 | 0.00 | 0.00 | 0.00 | 5.35 | 73.86 | 7.55 |
| 21 | — | — | 43.96 | 32.14 | 12.15 | 0.00 | 0.00 | 0.00 | 19.99 | 61.24 | 6.99 |
| 22 | — | — | 141.53 | 129.05 | 126.31 | 144.49 | 146.03 | 143.14 | 123.85 | 133.04 | 105.51 |

The features that more often resulted in large H-values were the maximum (F01), minimum (F02), mean (F03), variance (F05), ratio (F06), number of Gaussian peaks (F09), amplitude of the dominant valley and dominant peak (F10, F11), and the absolute error between the original data and the model Gaussian (F22). In particular, the absolute error between the original data and the model Gaussian (F22) appeared to yield strong results for all two-dimensional projections. In addition, features derived from the geometrically dominant transverse slice (GT) resulted in the largest number of features with H-values larger than 100 (11 of 42 features). Similar results were obtained from analysis of the derived features.

Summary of Kruskal-Wallis analysis of features from two-dimensional spectral analysis of scattering images are summarized in Table 6 (for projections 3-11). The results suggest that there were statistically significant differences between the spectral features of PIP joints of subjects with RA and PIP joints of subjects without RA. The features derived from the variance projections yielded the largest H-statistics.

Dunn's test was used to obtain insight into the differences between the six diagnosis groups. The critical Q-statistic value to establish statistically significant differences at the 0.05 and 0.01 significance levels was 2.936 and 3.403, respectively.

A trend became evident (Table 7). There were statistically significant differences between group H and all other groups (Q>2.936). However, differences between groups A, B, C, D, and E were not statistically significant (Q<2.936). For example, the results from Dunn's test applied to six features derived from two-dimensional spectral analysis are shown in Table 7, where Q>2.936 when H was compared to any other group (A, B, C, D, or E). However, Q<0.95 when any of the unhealthy groups were compared was to each other, suggesting that there are groups A, B, C, D, and E were not statistically different. However, the differences between subjects in Group H and all other groups were statistically significant. Similar results were obtained from all other features.

TABLE 6

H-statistics from Kruskal-Wallis ANOVA test results using features derived from 2D FFT of $\mu_s'$ images.

| Feature | SS | SC | ST | VS | VC | VT | GS | GC | GT |
|---|---|---|---|---|---|---|---|---|---|
| 23 | 22.36 | 22.36 | 22.36 | 144.95 | 145.95 | 142.47 | 12.46 | 22.23 | 20.80 |
| 24 | 122.99 | 65.59 | 122.99 | 142.74 | 138.56 | 139.92 | 114.76 | 66.54 | 69.22 |
| 25 | 65.59 | 67.92 | 67.92 | 136.98 | 134.00 | 130.21 | 72.42 | 126.21 | 62.54 |
| 26 | 82.30 | 57.06 | 119.33 | 133.84 | 119.70 | 124.50 | 89.99 | 55.61 | 61.22 |
| 27 | 63.41 | 58.45 | 109.46 | 135.40 | 114.97 | 125.64 | 73.85 | 61.05 | 77.00 |
| 28 | 116.73 | 62.42 | 116.73 | 131.72 | 99.78 | 132.09 | 125.15 | 76.04 | 78.80 |
| 29 | 62.42 | 46.67 | 46.67 | 95.79 | 136.01 | 133.50 | 47.32 | 36.57 | 67.19 |
| 30 | 82.97 | 77.78 | 124.99 | 122.72 | 105.96 | 108.28 | 89.70 | 49.50 | 53.51 |
| 31 | 70.41 | 65.03 | 123.47 | 120.00 | 111.32 | 111.60 | 63.06 | 59.97 | 81.82 |
| 32 | 73.25 | 65.26 | 60.59 | 90.47 | 128.72 | 129.57 | 70.64 | 55.66 | 63.59 |
| 33 | 70.20 | 42.49 | 41.91 | 96.32 | 129.84 | 131.19 | 68.36 | 44.44 | 71.79 |
| 34 | 74.08 | 61.71 | 81.21 | 99.21 | 107.28 | 113.73 | 89.00 | 49.60 | 63.75 |
| 35 | 71.51 | 78.79 | 75.86 | 96.23 | 97.80 | 120.42 | 85.57 | 77.66 | 81.85 |

TABLE 7

Q-statistic from Dunn's test on sample features from 2D FFT.

| Groups to Compare | F23:VS:a | F24:VS:a | F25:VS:a | F23:VS:s | F24:VS:s | F25:VS:s |
|---|---|---|---|---|---|---|
| H vs A | 5.10 | 5.17 | 5.18 | 6.13 | 6.45 | 6.34 |
| H vs B | 6.35 | 6.41 | 6.36 | 6.29 | 5.92 | 6.36 |
| H vs C | 4.74 | 4.74 | 4.77 | 5.84 | 5.43 | 5.37 |
| H vs D | 7.32 | 7.41 | 7.39 | 8.09 | 8.00 | 8.04 |
| H vs E | 5.98 | 6.04 | 5.98 | 6.52 | 6.88 | 6.91 |
| A vs B | 0.95 | 0.94 | 0.89 | 0.12 | 0.40 | 0.02 |
| A vs C | 0.39 | 0.35 | 0.36 | 0.58 | 0.04 | 0.07 |
| A vs D | 0.89 | 0.89 | 0.87 | 0.57 | 0.24 | 0.37 |
| A vs E | 0.15 | 0.14 | 0.09 | 0.29 | 0.29 | 0.18 |
| B vs C | 0.46 | 0.50 | 0.43 | 0.48 | 0.40 | 0.05 |
| B vs D | 0.15 | 0.14 | 0.11 | 0.44 | 0.68 | 0.35 |
| B vs E | 0.86 | 0.87 | 0.86 | 0.42 | 0.14 | 0.20 |
| C vs D | 0.36 | 0.41 | 0.37 | 0.13 | 0.17 | 0.25 |
| C vs E | 0.28 | 0.24 | 0.30 | 0.88 | 0.30 | 0.23 |
| D vs E | 0.80 | 0.81 | 0.84 | 0.95 | 0.59 | 0.60 |

Group means and standard error bars were plotted to highlight the observed differences between groups A-H for four particular features (FIG. 10(a) through FIG. 10(d)). The error bars around the average within-group mean showed that only the interval belonging to the healthy subjects was disjoint from the rest of the groups. These observations are consistent with results from Dunn's test. The variance in the scattering coefficients (F06:UV:s) was significantly larger in the joints of healthy subjects (FIG. 10(a)). This suggested that the optical properties in the PIP joints of patients with RA, compared to healthy patients, were more homogeneously distributed. The cross section VT, which represents the variance across all transverse cross-sections, was an important projection. The mean of the scattering coefficient in this projection (F03:VT:s) was significantly larger for healthy patients (FIG. 10(b)). Within this projection, the magnitude of the dominant Gaussian (F11:VT:s) was larger for patients with healthy fingers (FIG. 10(c)). The total error between the original data and the Gaussian model data (F22:VT:s) was larger for healthy patients (FIG. 10(d)). This occurred because the scattering coefficient was more homogenous within this projection for patients with RA, and it is therefore easier to find a Gaussian function that accurately models this data. Examples of the Youden index obtained from ROC curve analysis using and derived features are presented in Tables 8 and 9. The value of Youden indices ranges from 0.0 to a maximum of 0.83.

For example, the results from ROC analysis of the two-dimensional spectral features of the scattering coefficient are presented in Table 8. The largest Youden index was 0.83, while the smallest Youden index was 0.59. Two separate features were responsible for this value. In both cases, it was the coefficient of the lowest Fourier frequency that served as a good classifier. In addition, the best single feature classifiers all were derived from projections 6, 7, and 8 (the variance projections).

The performance of the summation projections (projections 2-4) and the geometrically dominant slices (projections 9-11) performed poorly in comparison. The Youden index varied from 0.12 to 0.76 and 0.06 to 0.77, respectively. These results imply that the projection of the three-dimensional data into two-dimensional variance projections can yield strong results.

TABLE 8

ROC analysis results using features derived from 2D FFT of $\mu'_s$ images.

| Feature | SS | SC | ST | VS | VC | VT | GS | GC | GT |
|---|---|---|---|---|---|---|---|---|---|
| 23 | 0.12 | 0.12 | 0.12 | 0.83 | 0.83 | 0.81 | 0.06 | 0.12 | 0.07 |
| 24 | 0.73 | 0.55 | 0.73 | 0.82 | 0.79 | 0.81 | 0.69 | 0.56 | 0.50 |
| 25 | 0.55 | 0.51 | 0.51 | 0.77 | 0.75 | 0.74 | 0.50 | 0.76 | 0.46 |
| 26 | 0.58 | 0.51 | 0.72 | 0.74 | 0.69 | 0.71 | 0.61 | 0.49 | 0.45 |
| 27 | 0.49 | 0.48 | 0.67 | 0.76 | 0.67 | 0.72 | 0.52 | 0.46 | 0.50 |
| 28 | 0.73 | 0.53 | 0.73 | 0.74 | 0.59 | 0.77 | 0.77 | 0.54 | 0.55 |
| 29 | 0.53 | 0.44 | 0.44 | 0.63 | 0.80 | 0.78 | 0.51 | 0.33 | 0.48 |
| 30 | 0.57 | 0.57 | 0.76 | 0.71 | 0.64 | 0.66 | 0.55 | 0.47 | 0.42 |
| 31 | 0.56 | 0.53 | 0.72 | 0.70 | 0.66 | 0.65 | 0.51 | 0.45 | 0.57 |
| 32 | 0.61 | 0.49 | 0.48 | 0.63 | 0.77 | 0.78 | 0.58 | 0.44 | 0.47 |
| 33 | 0.53 | 0.35 | 0.42 | 0.62 | 0.72 | 0.79 | 0.59 | 0.43 | 0.54 |
| 34 | 0.55 | 0.49 | 0.53 | 0.63 | 0.66 | 0.71 | 0.63 | 0.41 | 0.45 |
| 35 | 0.52 | 0.56 | 0.55 | 0.63 | 0.59 | 0.71 | 0.62 | 0.55 | 0.58 |

TABLE 9

ROC analysis results using features derived from 3D FFT of $\mu'_s$ images.
Feature Number

| 36-42 | 43-49 | 50-56 | 57-63 | 64-70 | 71-78 | 77-84 | 85-91 | 92-97 |
|---|---|---|---|---|---|---|---|---|
| 0.12 | 0.72 | 0.73 | 0.57 | 0.35 | 0.54 | 0.52 | 0.49 | 0.58 |
| 0.73 | 0.67 | 0.53 | 0.76 | 0.57 | 0.49 | 0.49 | 0.49 | 0.52 |
| 0.55 | 0.48 | 0.44 | 0.72 | 0.46 | 0.54 | 0.53 | 0.48 | 0.59 |
| 0.51 | 0.50 | 0.57 | 0.53 | 0.52 | 0.48 | 0.55 | 0.52 | 0.46 |
| 0.58 | 0.50 | 0.56 | 0.49 | 0.54 | 0.42 | 0.56 | 0.50 | 0.55 |
| 0.49 | 0.52 | 0.61 | 0.48 | 0.49 | 0.45 | 0.51 | 0.59 | 0.50 |
| 0.51 | 0.45 | 0.53 | 0.42 | 0.44 | 0.55 | 0.50 | 0.53 | 0.57 |

Results from ROC analysis of three-dimensional spectral features from scattering images are presented in Table 9. The Youden index ranges from 0.12 to 0.76. The low frequency coefficients (first four columns) produced the largest Youden indices. However, the lowest Youden indices were also produced by coefficients that were derived from low frequencies. In general, two-dimensional projections of the variance across the three dimensional data produced the best individual classifiers.

A basic framework for extracting features from optical tomographic images was presented. The general process included three steps: (1) feature extraction, (2) statistical analysis of individual features, and (3) ROC curve analysis of features that show statistically significant differences between groups.

Feature extraction involved projecting the reconstructed data onto multiple two- and three-dimensional spaces, then the distribution of the optical parameters was quantified through statistical analysis, parameterization of the distributions, and spectral analysis.

Statistical analysis of the extracted features was used to discover which features revealed statistically significant differences between diagnosis groups. This analysis allowed testing of the null hypothesis. Then, evaluation of the strength of individual features as classifiers was performed with one-dimensional ROC curve analysis. On features that allowed rejection of the null hypothesis needed to be considered in this step. A group of best "one-dimensional" classifiers can then be chosen from ROC analysis. This set of features can be used in multidimensional classification.

The best weak classifiers were chosen using the strategy presented above. The 72 features that resulted in the largest Youden index from one-dimensional ROC curve analysis were chosen (Table 10 below). We chose the top 32 features from the statistical analysis and parameterization procedure (16 features from and, respectively). Then, we chose the top 15 classifiers from two- and three-dimensional spectral analysis, respectively (15 features from and, respectively).

TABLE 10

List of the best weak classifiers from ROC analysis

| Feature Number | Shorthand Name |
|---|---|
| 1 | F01:UV:a |
| 2 | F02:UV:a |
| 3 | F03:UV:a |
| 4 | F06:UV:a |
| 5 | F07:UV:a |
| 6 | F07:SV:a |
| 7 | F07:ST:a |
| 8 | F03:VS:a |
| 9 | F01:VC:a |
| 10 | F03:VC:a |
| 11 | F01:VT:a |
| 12 | F03:VT:a |
| 13 | F07:VT:a |
| 14 | F07:FT:a |
| 15 | F22:SS:a |
| 16 | F22:VS:a |
| 17 | F11:VC:a |
| 18 | F22:VC:a |
| 19 | F11:VT:a |
| 20 | F22:VT:a |
| 21 | F11:GC:a |
| 22 | F01:UV:s |
| 23 | F02:UV:s |
| 24 | F03:UV:s |
| 25 | F06:UV:s |
| 26 | F07:UV:s |
| 27 | F07:SV:s |
| 28 | F07:ST:s |
| 29 | F03:VS:s |
| 30 | F01:VC:s |
| 31 | F03:VC:s |
| 32 | F01:VT:s |
| 33 | F03:VT:s |
| 34 | F07:VT:s |
| 35 | F07:FT:s |
| 36 | F22:SS:s |
| 37 | F22:VS:s |
| 38 | F11:VC:s |
| 39 | F22:VC:s |
| 40 | F11:VT:s |
| 41 | F22:VT:s |
| 42 | F11:GC:s |
| 43 | F23:VC:s |
| 44 | F23:VS:s |
| 45 | F24:VS:s |
| 46 | F24:VT:s |

TABLE 10-continued

List of the best weak classifiers from ROC analysis

| Feature Number | Shorthand Name |
|---|---|
| 47 | F23:VT:s |
| 48 | F29:VC:s |
| 49 | F33:VT:s |
| 50 | F24:VC:s |
| 51 | F32:VT:s |
| 52 | F29:VT:s |
| 53 | F25:VS:s |
| 54 | F28:VT:s |
| 55 | F28:GS:s |
| 56 | F32:VC:s |
| 57 | F30:ST:s |
| 58 | F58:SV:s |
| 59 | F37:SV:s |
| 60 | F50:SV:s |
| 61 | F59:SV:s |
| 62 | F43:SV:s |
| 63 | F44:SV:s |
| 64 | F51:SV:a |
| 65 | F56:SV:a |
| 66 | F74:SV:a |
| 67 | F61:SV:s |
| 68 | F55:SV:s |
| 69 | F88:SV:a |
| 70 | F94:SV:s |
| 71 | F90:SV:s |
| 72 | F71:SV:a |

In general, supervised multiparameter classification algorithms seek to determine a boundary that best separates two (or more) distinct groups of data. Here, we considered a two-class problem, where the classes were affected or not affected.

There were two distinct aspects to this process: (1) training the classification algorithm and (2) testing the generalization of the classifier. Here, we employed the leave-n-out method to train and test the classifier.

In the first step the data set was divided into two disjoint subsets: (1−n) % of the data was used to train the classifier, while the remaining n % was used to test the ability of the classifier to accurately classify new data. The training phase used the training data to determine the boundary that best separated the two classes. The testing phase used the testing data to determine the ability of the decision boundary to accurately classify new data.

The testing data was composed of 10% of the total data (i.e. 22 distinct PIP joint images in the case of classification of RA images). The training data was chosen randomly from the entire data set, with the only condition being that there was at least one data point from the affected and healthy groups. This process was repeated 100 times to remove any possible bias that can arise when only easily separable data was used for testing.

$$Se = \frac{TP}{TP + FN} \quad (11)$$

$$Sp = \frac{TN}{TN + FP}$$

$$Y = Se + SP - 1$$

The number of true negatives (TN), true positives (TP), false negatives (FN), and false positives (FP) were recorder for all iterations. From these results, the sensitivity (Se), specificity (Sp), and Youden index (Y) were computed for all iterations.

TABLE 10

List of the best weak classifiers from ROC analysis

| Feature Number | Shorthand Name |
|---|---|
| 1 | F01:UV:a |
| 2 | F02:UV:a |
| 3 | F03:UV:a |
| 4 | F06:UV:a |
| 5 | F07:UV:a |
| 6 | F07:SV:a |
| 7 | F07:ST:a |
| 8 | F03:VS:a |
| 9 | F01:VC:a |
| 10 | F03:VC:a |
| 11 | F01:VT:a |
| 12 | F03:VT:a |
| 13 | F07:VT:a |
| 14 | F07:FT:a |
| 15 | F22:SS:a |
| 16 | F22:VS:a |
| 17 | F11:VC:a |
| 18 | F22:VC:a |
| 19 | F11:VT:a |
| 20 | F22:VT:a |
| 21 | F11:GC:a |
| 22 | F01:UV:s |
| 23 | F02:UV:s |
| 24 | F03:UV:s |
| 25 | F06:UV:s |
| 26 | F07:UV:s |
| 27 | F07:SV:s |
| 28 | F07:ST:s |
| 29 | F03:VS:s |
| 30 | F01:VC:s |
| 31 | F03:VC:s |
| 32 | F01:VT:s |
| 33 | F03:VT:s |
| 34 | F07:VT:s |
| 35 | F07:FT:s |
| 36 | F22:SS:s |
| 37 | F22:VS:s |
| 38 | F11:VC:s |
| 39 | F22:VC:s |
| 40 | F11:VT:s |
| 41 | F22:VT:s |
| 42 | F11:GC:s |
| 43 | F23:VC:s |
| 44 | F23:VS:s |
| 45 | F24:VS:s |
| 46 | F24:VT:s |
| 47 | F23:VT:s |
| 48 | F29:VC:s |
| 49 | F33:VT:s |
| 50 | F24:VC:s |
| 51 | F32:VT:s |
| 52 | F29:VT:s |
| 53 | F25:VS:s |
| 54 | F28:VT:s |
| 55 | F28:GS:s |
| 56 | F32:VC:s |
| 57 | F30:ST:s |
| 58 | F58:SV:s |
| 59 | F37:SV:s |
| 60 | F50:SV:s |
| 61 | F59:SV:s |
| 62 | F43:SV:s |
| 63 | F44:SV:s |
| 64 | F51:SV:a |
| 65 | F56:SV:a |
| 66 | F74:SV:a |
| 67 | F61:SV:a |
| 68 | F55:SV:s |
| 69 | F88:SV:s |
| 70 | F94:SV:s |
| 71 | F90:SV:s |
| 72 | F71:SV:a |

The results we report are the average Se, Sp, and Y index across all iterations. Unless otherwise indicated, the standard deviations for the Se and Sp were less than 3% for all results.

The KNN algorithm classifies each unseen feature vector, x, according to the density of affected or healthy points within a neighborhood r (encompassing a maximum of k neighbors). Specifically, every feature vector x in the testing set should be classified according to the following rules.

1. Identify the k nearest neighbors, according to the Euclidean distance measure, out of all the training vectors, regardless of class label. (k is chosen to be odd for a two class problem, and in general not to be a multiple of the number of classes M).
2. Out of these k samples, identify the number of training vectors ( ) that belongs to class, where i=1, . . . , M.
3. Assign x to the class with the maximum number of samples.

The choice of k has an effect on results of classification: generally, larger values reduce the effect of noise, but make boundaries between classes less distinct. The simplest version of the algorithm is for k=1, known as the nearest neighbor (NN) rule. In other words, a feature vector x is assigned to the class of its nearest neighbor. The classification efficiency of the KNN algorithm when k varies will be evaluated.

In general, for classification with discriminant analysis, the posterior probability $p(\omega_i|x)$ of feature vector x originating from class is defined by Bayes theorem, $$p(\omega_i | x) = \frac{p(x | \omega_i)P(\omega_i)}{P(x)}, \quad (12)$$

where $p(\omega_i|x)$ and $P(x)$ represent the prior probabilities for class and feature vector x, respectively. The classification is done using the maximum a posteriori estimate, $$\max_{\omega_i} \hat{p}(\omega_i | x) \quad (13)$$

and setting the prior probability for each feature vector equal, $$\hat{p}(\omega_i|x) \propto \hat{p}(x|\omega_i)P(\omega_i) \quad (14)$$

In this study, the prior probabilities for each class were defined to be equal, so that the classification depended only on the likelihood function estimate. Furthermore, the likelihood functions are assumed to follow the general multivariate normal distribution, $$p(x | \omega_i) = \frac{1}{(2\pi)^{l/2}|\Sigma_i|^{1/2}} \exp\left[-\frac{1}{2}(x - \vec{\mu_i})^T \Sigma_i^{-1}(x - \vec{\mu_i})\right], \quad (15)$$

$$i = 1, \ldots, M,$$

where l is the dimensionality of x, M is the number of possible classes (here M=2), represents the mean value, and represents the covariance matrix of class. Estimates for the mean and the covariance matrix are computed from the training data, using the maximum likelihood estimation.

For classification purposes, the training data is used to estimate) and for each class. Using Bayes rule, the classification is then performed using discriminant functions $$g_i(x) = \ln(p(x)|\omega_i)P(\omega_i)) \quad (16)$$

where $P(\omega_i)$ is the a priori probability of class. Here, the assumption that $P(\omega_i)=P(\omega_j) \forall i,j$ was used. The decision surfaces resulting from the discriminant functions are $g_i(x)-g_j(x)=0$.

In a general case, the associated decision curves are hyperquadratics, and the classification task is called quadratic discriminant analysis. However, by making different assumptions on the covariance matrix estimates the decision curves can be modified, resulting in different classification outcomes. In this study, two alternative discriminant analysis methods were used:

1. Linear Naive-Bayes classifier: Covariance matrices are assumed to be the same in each class ($\Sigma_i=\Sigma_j \forall i,j$), resulting in decision surfaces that are hyperplanes. The individual features are assumed to be statistically independent, resulting in diagonal covariance matrix estimates.
2. Quadratic Naive-Bayes classifier: The general version, the covariance matrix for each class is estimated and the individual features are assumed to be statistically independent, resulting in diagonal covariance matrix estimates. The resulting classification boundaries are hyperquadratics.

SOMs were used to perform image classification in multidimensional feature space, varying the number of neurons and learning rate used for pattern learning. The total neurons were varied between 6, 10, 16, and 20. The learning rate was varied from 0.01, 0.1, and 1.0.

The SVM algorithm was implemented for the general two-class problem, where the classes are not necessarily linearly separable. The optimal separating line (hyperplane in n-dimensional space), H, is denoted. The optimal separating hyperplane is attained by maximizing the margin, which can be re-written as a function of the separating plane as $m=2/|\omega|$. Then, the primal SVM is a quadratic program were maximizing the margin corresponds to minimizing $|\omega|$ and can be written as $$\min_{\omega,b,\xi} \max_{\alpha \geq 0, \beta \geq 0} \left( \frac{1}{2}\|w\|^2 + C\sum_i \xi_i - \sum_i \alpha_i(y_i(w^T x_i + w_0) - 1 + \xi_i) - \sum_i \beta_i \xi_i \right) \quad (17)$$

Where $\xi_i$ are "slack" variables that allow for handling of non-separable data points, C is a penalty cost associated with misclassified data points, and $\alpha$ and $\beta$ are Lagrange multipliers. Then, the dual is obtained by finding the gradient of the quadratic program with respect to all variables ($\omega$, b, and $\xi_i$) and combining the results with the non-negativity constraints on the Lagrange multipliers $\alpha$ and $\beta$. The dual SVM for the non-separable two-class case can then be written as $$L_D : \max_{\alpha \geq 0} \left( \sum_i \alpha_i - \frac{1}{2} \sum_i \sum_j \alpha_i \alpha_j y_i y_j k(x_i, x_j) \right) \quad (18)$$

subject to $\quad (19)$ $$\sum_i \alpha_i y_i = 0,$$

$$\alpha_i \in [0, C]$$

Where the kernel is a function that takes two input vectors and computes a scalar product, $k(x, y)=\phi(x)^T \phi(y)$. This is popularly known as the "kernel" trick and defines the type of separating hyperplane used for classification. This quadratic program is solved for. Subsequently, the optimal separating hyperplane can be recovered from one of the constraints, and classification is done using the scheme. The value of b is found from only those data vectors that are on the margin (i.e. the support vectors). The support vectors correspond to vectors with non-zero and not-C $\alpha$'s and by assuming $\xi_i=0$. The, $b=\bar{b}$, where b is computed from $y_i(\omega^T x_i - \bar{b}_i) - 1 + \xi_i = 0$.

Thus, any data point (or feature vector) x can be classified using the above scheme, where $f(x)=\pm 1$ states whether data point x is classified into class +1 or −1.

The kernel trick is very useful as it allows classification with non-linear hyperplanes. It allows mapping of a d-dimensional input vector from L-space into a higher dimensional H (Hilbert) feature-space using the basis function $\Phi$, such that $x_i \to \Phi(x_i)$. There are many kernel functions that can be implemented. In this work we implemented the linear, quadratic, polynomial, and radial basis functions (RBF) kernels. The linear kernel is trivial. The other kernels are listed below.

$$k(x, y) = (x_1 y_1 + x_2 y_2)^2 \quad (20)$$

$$k(x, y) = (x^T y + 1)^p \quad (21)$$

$$k(x, y) = \exp\left(-\frac{1}{2\sigma^2} \|x - y\|^2\right) \quad (22)$$

Determination of the optimal set of features was achieved by developing an evolution strategy algorithm (similar to simulated annealing). Generally referred to as $(1, \lambda)$ single parent evolution strategy (ES), it is an optimization technique. Any of a variety optimization strategies and algorithms may be used. The evolution strategy used two steps; (1) mutation and (2) selection as its search operator. In the mutation step, $\lambda$ mutants are generated to compete with their parents. In the selection step, new parents are selected from the set of previous generation parents and their $\lambda$ mutants. The selection is made only based on the fitness ranking, not on the actual fitness values. Usually the operator is applied in a loop. An iteration of the loop is called a generation. The sequence of generations is continued until a termination criterion is met.

The $(1, \lambda)$ evolution strategy may be used to select feature combinations based on highest Youden (Y) indices. A process is summarized as follows:

1. An initial feature combination is chosen as the first generation parents.
2. All possible mutants are generated by adding, dropping, or replacing one feature from the parent combination.
3. Of all the mutants and their parent, the combination with the highest Youden index becomes the parent in next generation.
4. Repeat this process until the Youden index cannot be improved.

This problem was cast as an optimization problem, where the objective function, $\phi_\lambda^k$, was defined as the as the average Youden index over N iterations of the kth set of feature combinations in the $\lambda$ generation.

$$\phi_{\lambda+1} \to \max_{\lambda,k} \phi_\lambda^k = \frac{1}{N} \sum_i^N (Se_i^k + Sp_i^k - 1) \quad (23)$$

The set of features that maximizes the objective function in the λ generation becomes the parents of the generation. This process guarantees that the sensitivities and specificities will increase with every new generation and that the solution will converge to a near optimal feature combination (a local maximum) that maximizes the objective function.

Two-dimensional feature combinations were tested. The set of features that yield the highest Youden indices were used as inputs to run the (1, λ) evolution algorithm independently. As examples, the top 5 sensitivities, specificities, and feature combination to which the algorithm converged are disclosed.

Classification with KNN was performed using multiple neighboring points (k=1, 3, 5, 7, 10, 15, 20). For each value of k five optimization runs, each with distinct seed features, were executed. This resulted in a total of 7×5=35 distinct executions of the optimization algorithm. The results for the best 3 optimization runs for k=1, 5, 10, 15 are summarized in Table below. The results from the remaining optimization runs were well within the trend represented by the results presented in this section.

The highest Youden index obtained was 0.95 (0.95 Se, 1.00 Sp) using k=5, where the initial features were {37, 47} and the final features were {6, 13, 26, 37}. Convergence was achieved after 4 generations. In general KNN was able to achieve highly accurate classification results. In general, using few numbers of neighbors (i.e. k=1) or too many neighbors (k>15) resulted in marginally lower classification accuracy. Using a large number of neighbors (k>15) resulted in significantly lower classification accuracy.

TABLE 11

Evolution strategy results from KNN

| k | Se | Sp | Y | Initial Combination | Final Combination | Steps |
|---|------|------|------|---------|------------------|---|
| 1 | 0.96 | 0.97 | 0.93 | 1, 57 | 1, 24, 26, 37, 57 | 4 |
|   | 0.96 | 0.96 | 0.92 | 1, 58 | 1, 25, 37, 43, 58 | 4 |
|   | 0.97 | 0.95 | 0.92 | 21, 58 | 17, 21, 26, 28, 58 | 4 |
| 5 | 0.95 | 1.00 | 0.95 | 37, 47 | 6, 13, 26, 37 | 4 |
|   | 0.95 | 0.99 | 0.94 | 26, 37 | 6, 7, 26, 37 | 3 |
|   | 0.96 | 0.98 | 0.94 | 24, 26 | 6, 13, 26, 37 | 5 |
| 10 | 0.96 | 0.97 | 0.93 | 24, 26 | 11, 26, 27, 31, 33, 37 | 8 |
|   | 0.98 | 0.94 | 0.92 | 21, 38 | 37, 38, 39 | 5 |
|   | 0.95 | 0.97 | 0.92 | 26, 37 | 12, 26, 37 | 2 |
| 15 | 0.97 | 0.95 | 0.92 | 10, 33 | 1, 10, 26, 29, 30, 33 | 5 |
|   | 0.97 | 0.94 | 0.91 | 26, 37 | 1, 7, 37 | 3 |
|   | 0.92 | 0.98 | 0.90 | 37, 49 | 5, 26, 49 | 4 |

Figure 11:
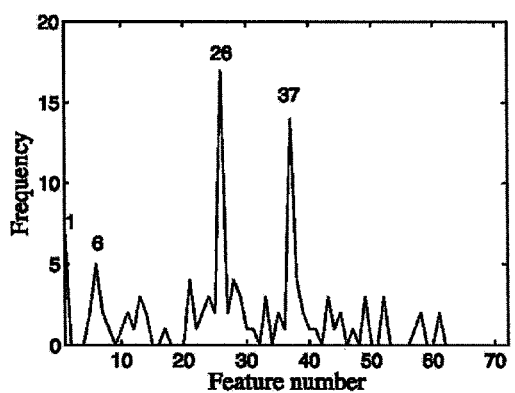
FIG. 11(a) shows a frequency distribution representing instances that certain features appear as optimal classifiers.
FIG. 11(b) shows a progressive path indicating Youden index representing an optimization strategy.
Figure 11:
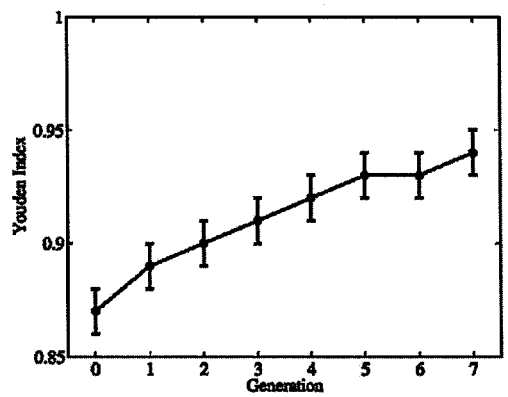

The frequency with which features appear as optimal classifiers (FIG. 11(a)) shows that features 1, 6, 26, and 37 appeared most often as optimal classifiers; each feature appeared in 7, 5, 27, and 14 distinct times as optimal classifier throughout all 35 executions of the optimization algorithm.

An example of the path taken by the evolution strategy is provided for visualization purposes (FIG. 11(b)); the path corresponds to run 1 with k=10. The initial features {24, 26} achieved a Youden index of 0.87 (0.96±0.01 Se, 0.91±0.02 Sp) and evolved to features {11, 26, 27, 31, 33, 48} after 6 generations. The final Youden index was 0.93 (0.96±0.01 Se, 0.97±0.02 Sp). The evolution of the features was as follows: {24, 26}, {24, 26, 31}, {26, 29, 31}, {26, 27, 29, 31}, {11, 26, 27, 29, 31}, {11, 26, 27, 29, 31, 48}, and {11, 26, 27, 31, 33, 48}.

Figure 12A:
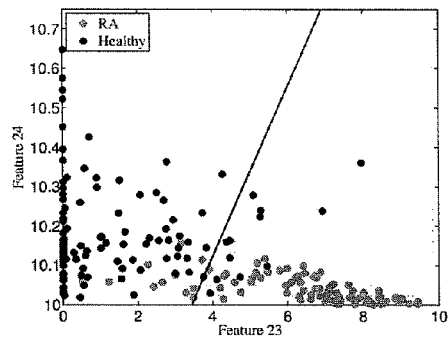
FIGS. 12A and 12B show examples of result presentation output formats for presenting classification results to a user.
Figure 12B:
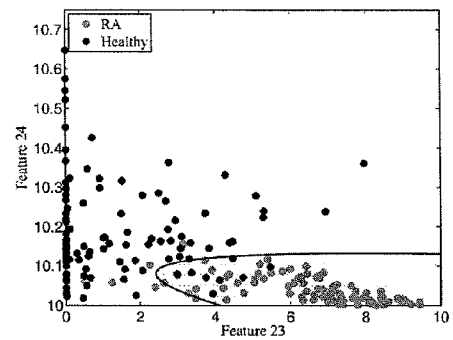
Figure 12C:
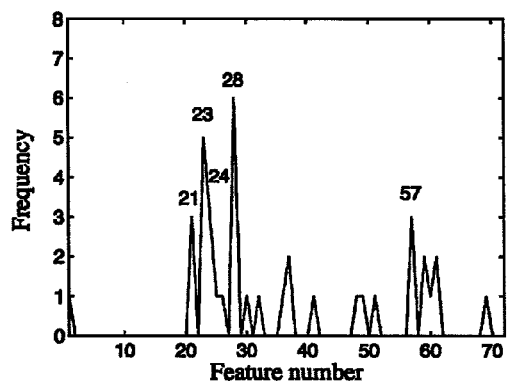
FIGS. 12C and 13A show frequency distributions representing instances that certain features appear as optimal classifiers.
Figure 12D:
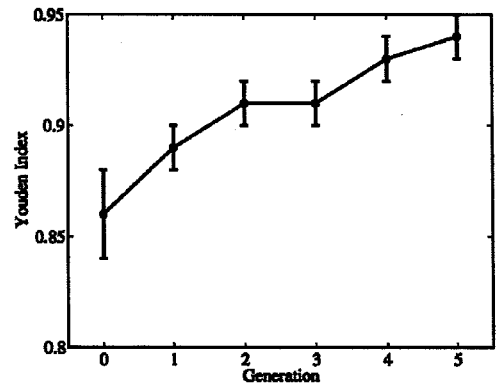
FIGS. 12D and 13B show a progressive paths indicating Youden index representing an optimization strategy.

DA classification was performed with linear (LDA) and quadratic (QDA) decision boundaries. 5 distinct runs were executed for each type of DA, where the initial set of features was different for each run. Results from the best 3 results from each type of DA are summarized in Table 12. To help visualize the division boundaries for each type of DA we have provided example of linear and quadratic decision boundaries (FIGS. 12A and 12B, respectively). FIG. 12C shows the frequency with which all features appeared as optimal classifiers and FIG. 12D shows examples of an evolutionary path for LDA.

Youden indices up to 0.95 (98% Se, 97% Sp) and 0.93 (98% Se, 95% Sp) were achieved with LDA and QDA, respectively. In the case of Y=0.95 (LDA, run 1), the initial features were {23, 24}, while the final features combination was {23, 24, 49, 61}. The optimization algorithm took 5 generations to converge. The final set of features included basic statistical features, {23, 24}, as well as coefficients from the two- and three-dimensional Fourier transform of the data, {49, 61}.

TABLE 12

Evolution strategy results from DA

| DA | Se | Sp | Y | Initial Combination | Final Combination | Steps |
|---|------|------|------|---------|------------------|---|
| Linear | 0.98 | 0.97 | 0.95 | 23, 24 | 23, 24, 49, 61 | 5 |
|   | 0.97 | 0.97 | 0.94 | 37, 38 | 1, 24, 28, 37, 51 | 6 |
|   | 0.95 | 0.98 | 0.94 | 23, 61 | 23, 24, 61, 70 | 3 |
| Quadratic | 0.98 | 0.95 | 0.93 | 28, 40 | 21, 28, 30, 59 | 4 |
|   | 0.98 | 0.94 | 0.93 | 28, 36 | 21, 26, 28, 36, 57 | 5 |
|   | 0.96 | 0.95 | 0.92 | 23, 57 | 23, 41, 57, 60 | 3 |

In general, the number of features to which the optimization algorithm converged varied from 2 to 5. The algorithm failed to improve on the original set of feature only once (QDA, run 5). In most cases the optimal set of features included a combination of basic, parameterization, and spectral features. The features that appeared as optimal classifiers most often were features 21, 23, 24, 28, and 57; they appeared 3, 5, 4, 28, and 3 times each, respectively, throughout all 10 optimization runs. We note the most basic features previously studied in [3, 8] did not appear in the list of optimal features.

Figure 13A:
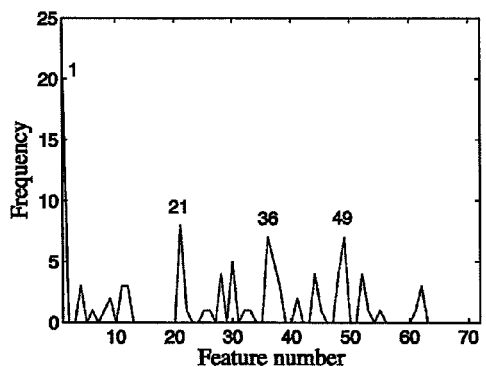
Figure 13B:
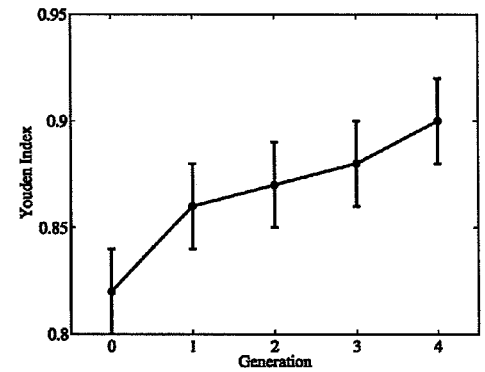

FIG. 13A shows frequency with which all features appeared as optimal classifiers. FIG. 13B shows an example of the evolution paths for SOM (n=9; l=1:0, run 2).

An example of a typical evolution path (FIG. 12D) is presented to highlight the improvements in sensitivity and specificity achieved with the evolution algorithm. In the example, the Youden index started at 0.86 (0.94±0.01 Se, 0.92±0.02 Sp) and, after 5 generations, evolved to 0.94 (0.97±0.01 Se, 0.97±0.01 Sp). The features evolved as follows: {37, 38}, {28, 37, 38}, {28, 37, 38, 49}, {24, 28, 37, 49}, {1, 24, 28, 37, 49}, {1, 24, 28, 37, 51}.

The optimization algorithm was executed for 5 distinct set of two dimensional seeds for each possible combinations of neurons (n=9, 16, 25) and learning rate (l=0.01, 0.1, 1.0), for a total of 9×5=45 optimization runs. Results from classification with SOMs are summarized in Table 4. While the number of neurons n used for classification did have an impact on the classification accuracy, we found that the learning rate 1 did not make a significant difference in performance of SOMs; for this reason only results that show the dependence on n are shown.

The frequency with which each individual feature appeared as an optimal classifier is also presented. The features that appeared as optimal classifiers most often were features 1, 21, 36, and 49; they appeared 20, 9, 8, and 8 times each, respectively, throughout all 48 optimization runs.

TABLE 13

Evolution strategy results from SOM

| n | Se | Sp | Y | Initial Combination | Final Combination | Steps |
|---|---|---|---|---|---|---|
| 9 | 0.96 | 0.96 | 0.92 | 1, 41 | 1, 45, 49 | 4 |
|  | 0.97 | 0.93 | 0.90 | 11, 30 | 21, 30, 48 | 5 |
|  | 0.95 | 0.94 | 0.89 | 39, 49 | 28, 44 | 3 |
| 16 | 0.92 | 0.96 | 0.88 | 11, 37 | 21, 36 | 3 |
|  | 0.93 | 0.94 | 0.87 | 9, 44 | 1, 52 | 3 |
|  | 0.92 | 0.95 | 0.87 | 1, 49 | 9, 48 | 4 |
| 25 | 0.93 | 0.93 | 0.86 | 1, 5 | 1, 37 | 2 |
|  | 0.92 | 0.94 | 0.86 | 28, 33 | 33, 38 | 2 |
|  | 0.92 | 0.93 | 0.85 | 36, 70 | 37, 70 | 2 |

A Youden index of up to 0.92 was achieved (0.96 Se, 0.96 Sp) using 9 neurons and l=1.0, where the initial features were {1, 41} and the optimal features converged to {1, 45, 49} after 4 generations. The performance of SOMs with 16 (Y=0.88) and 25 (Y=0.86) neurons was less accurate than with 9 neurons. This suggests that it is likely that using 16 or 25 neurons resulted in overfitting of the data.

In general, the evolution algorithm always converged in 2-4 generations (except in one case where it took 5 generations). Furthermore, the feature combinations that the algorithm always converged to were typically two-dimensional combinations (except in one case where it converged to three features). However, the optimal features were generally different from the initial features.

In the example of the evolution path, the Youden index evolved from 0.81 (0.92±0.01 Se, 0.89±0.02 Sp) to 0.90 (0.97±0.01 Se, 0.93±0.02 Sp) after 4 generations. The features evolved as follows: {11, 30}, {11, 30, 31}, {11, 30}, {11, 21, 30}, {21, 30, 48}. We note that the features in the 0th and 2nd generations are the same, and that this behavior occurs because of the stochastic nature of the evolution algorithm.

Classification with SVM was performed using a linear, quadratic, polynomial, and radial basis function (RBF) functions. Classification with the polynomial, kernel was explored with polynomials of degree 3, 4, 5, 6, and 7. The RBF kernel was explored by varying σ(0.1, 0.5, 1.0, 2, 5, 10.0). A total of 5 distinct classification runs (each with distinct features as seeds) were performed for each combination of kernel method and kernel parameter for a total of 5+5+5×5+5×6=65 distinct runs.

Results from classification with linear, quadratic, and polynomial kernel are summarized in Table 14. It is clear that linear, quadratic, and low order polynomials can separate the data very well. Classification accuracy with polynomials of higher order (p>=6) performed significantly worse than lower order polynomials. This was expected as it is well known that higher order polynomial can severely over-fit that data, resulting in poor cross validation results.

TABLE 14

Evolution strategy results from SVM

| SVM | Se | Sp | Y | Initial Combination | Final Combination | Steps |
|---|---|---|---|---|---|---|
| Linear | 0.99 | 0.98 | 0.97 | 1, 39 | 2, 21, 26, 37, 41 | 8 |
|  | 0.98 | 0.98 | 0.96 | 24, 48 | 23, 24, 29, 51, 58 | 5 |
|  | 0.99 | 0.97 | 0.96 | 1, 2 | 1, 2, 6, 26, 33 | 5 |
| Quadratic | 1.00 | 0.97 | 0.97 | 24, 48 | 17, 24, 26, 48, 62 | 4 |
|  | 0.99 | 0.98 | 0.97 | 1, 24 | 1, 2, 24, 26, 29, 66 | 7 |
|  | 0.95 | 0.99 | 0.94 | 2, 49 | 24, 25, 49 | 4 |

TABLE 14-continued

Evolution strategy results from SVM

| SVM | Se | Sp | Y | Initial Combination | Final Combination | Steps |
|---|---|---|---|---|---|---|
| Polynomial Order 3 | 0.99 | 0.99 | 0.98 | 24, 48 | 11, 24, 26, 43, 48 | 5 |
|  | 0.98 | 0.98 | 0.96 | 1, 2 | 1, 2, 26, 33, 67 | 4 |
|  | 0.97 | 0.99 | 0.95 | 23, 62 | 6, 23, 59, 60 | 6 |
| Polynomial Order 4 | 0.99 | 0.98 | 0.97 | 24, 52 | 11, 24, 26, 29, 52 | 5 |
|  | 0.98 | 0.95 | 0.93 | 7, 44 | 1, 23, 59 | 4 |
|  | 0.96 | 0.96 | 0.92 | 24, 48 | 16, 24, 39 | 4 |
| Polynomial Order 5 | 0.98 | 0.97 | 0.95 | 1, 24 | 1, 5 | 3 |
|  | 0.96 | 0.97 | 0.94 | 7, 37 | 1, 24, 37, 67 | 5 |
|  | 0.95 | 0.97 | 0.92 | 51, 62 | 28, 51, 52, 61 | 4 |

The number of features to which the optimization algorithm converged ranged from 2 to 6. The performance of the classifier decreased with increasing polynomial order, suggesting that the training data was being over fitted by high order polynomials. The longest optimization run was using a linear kernel, where the optimization step required 8 generations to converge to {2, 21, 26, 37, 41} and Youden index of 0.97 (0.99 Se, 0.98 Sp).

FIG. 14(a) shows SVM decision boundaries for optimal separation between features extracted from RA affected and healthy finger joints, respectively. The support vectors are denoted with a white dot. These were the optimization seeds that led to the largest specificity and sensitivity (Table 5). In this particular two-dimensional example there were 6 false positives and 9 false negatives (91% sensitivity and 95% specificity). There were 77 support vectors (36 from the RA class and 41 from the healthy class). FIG. 14(b) is a polynomial kernel of order 5 decision boundary for features 1, 5. This two-dimensional combination of features resulted in the highest sensitivity and specificity for any two-dimensional set of parameters (Table 5). In this example there were a total of 8 false positives and 5 false negatives (95% sensitivity and 93% specificity). There were 77 support vectors (36 from the RA class and 41 from the healthy class). FIG. 14(c) shows frequency with which all features appeared as optimal classifiers. FIG. 14(d) shows the evolution path of the objective function for the winning feature combination (from Table 5).

The best results are obtained with polynomial kernel of order 3. For that case the seed features were {24, 48} and the final set of features was {11, 24, 26, 43, 48}, resulting in a Youden index of 0.98 (0.99 Se, 0.99 Sp). For reference, the seed features and an example SVM decision boundary is presented in FIG. 14(a) (polynomial kernel of order 3). It is clear that the two seed features are strong classifiers because the data achieved good separability, although it is not yet completely separate.

There was one case where the optimization algorithm converged to a two-feature combination. The initial features were {1, 24} and the algorithm converged to features {1, 5} with Youden index of 0.95 (0.98 Se, 0.97 Sp) (FIG. 14(b)).

In general, the features that appeared most frequently as optimal classifier were 1, 2, 21, 23, 24, 25, 26, 37, and 52; each of these features appeared 18, 17, 14, 20, 19, 18, 17, and 14 times through all optimization runs using the linear, quadratic, and polynomial kernels (total of 35 runs) (FIG. 14(c)). This set optimum features included basic features from various data projections as well as frequency coefficients from two-dimensional data projections.

An example of the evolution of the Youden index over one execution of the evolution algorithm is presented in FIG. 14(d), corresponding to run 1 of the linear SVM kernel. In this example the initial Youden index was 0.87 (0.94±0.02 Se, 0.93±0.02 Sp) and converged, after 7 generations, to 0.97 (0.99±0.01 Se, 0.98±0.01 Sp). The evolution of the features occurred as follows: {1, 39}, {1, 2}, {1, 2, 26}, {1, 2, 26, 68}, {1, 2, 26, 72}, {1, 2, 26, 37}, {1, 2, 26, 37, 41}, {2, 21, 26, 37, 41}. In this example none of the seed features remained in the final set of features. In general, the optimal set of features contained at least one of the two initial features.

Accurate classification was also obtained when the RBFn kernel was used. The results suggest that an RBF with a σ=3 is the best RBF kernel. The classifier achieved 98% specificity and 99% sensitivity with initial feature {23, 62} and final features {16, 23, 24, 49, 60}. Overall, the maximum sensitivity and specificity values were increase by 5-10% by using the optimization algorithm with SVM.

These results are evidence that physiological changes to the PIP joints triggered by the onset of RA allow highly accurate diagnosis of the disease from FD-DOT images. The distribution and values of the absorption and scattering optical properties in the PIP joints of subjects with RA were significantly different from joints of subjects without RA. These differences allowed very accurate classification of each joint.

The highly accurate classification results presented in this work imply that through OT imaging and with CAD tools we can duplicate the diagnosis accuracy achieved through clinical evaluation. This is important, as it proves that OT imaging can be useful in diagnosing RA. Furthermore, the classification accuracy achieved in this work exceeds the classification accuracy achieved by x-ray imaging, MRI, and ultrasound in the diagnosis of RA. Furthermore, these methods could also be deployed in the diagnosis of other diseases with OT, including breast cancer and peripheral artery disease.

The technique can include a feature extraction part and an image classification part. In the feature extraction part optical tomographic (OT) images are "mined" for features that describe the distribution of tissue optical properties, such as absorption and scattering coefficient densities. These features can include, but are not limited to, statistical features, Gaussian mixture model parameters, spectral features, and wavelet coefficients. Statistical analysis of the extracted features can then be used to determine the utility of each extracted feature (i.e., which features actually show differences between healthy patients and affected patients). In the image classification part, supervised machine learning can be performed, where classification algorithm is 'trained" to differentiate between features derived from OT images of healthy patients and OT images of patients with a disease (rheumatoid arthritis is provided as an example). The algorithm can then be used to classify any future image.

Additionally, methods for obtaining information regarding a tissue are also disclosed. The methods can include generating an image which includes first data regarding absorption and scattering coefficients of the tissue based on radiation exiting from the at least one tissue; obtaining additional data based on the absorption and scattering coefficients from the image; and analyzing the additional data to determine or characterize anatomical and/or physiological indicators, such as, but not limited to, rheumatoid arthritis, associated with the tissue.

In embodiments, the additional data can include at least one of $\min(\mu_a)$, $\max(\mu_a)$, $\text{ratio}(\mu_a)$, $\text{var}(\mu_a)$, $\min(\mu_s)$, $\max(\mu_s)$, $\text{ratio}(\mu_s)$, or $\text{var}(\mu_s)$, combination of $\max(\mu_s)$ and $\text{ratio}(\mu_s)$, statistical features, Gaussian mixture model parameters, Fourier transform parameters, spectral features, and wavelet coefficients.

Embodiments of present disclosure also provide a non-transitory computer readable medium, which can include instructions thereon that are accessible by a hardware processing arrangement. When the processing arrangement executes the instructions, the processing arrangement can be configured to generate an image which includes data regarding absorption and scattering coefficients of the tissue based on electro-magnetic radiation exiting from the tissue; obtain additional data based on the absorption and scattering coefficients from the image; and analyze the additional data to determine or characterize an anatomical and/or physiological indicator associated with the tissue.

Since much of the disclosure in the present application has centered on a particular example of detecting RA, a diffusion and scattering coefficients have been disclosed as the detectable and quantifiable parameter of interest. It will be understood, however, that discrete optical tomography may be used to detect physiological characteristics, contrast agents, and other materials in the body. Also, the distribution need not be static. FIGS. 15A and 15B show the evolution of a spatial distribution of a physiological property over time in an imaged body part. At time $t_1$, a body part 402 contains a distribution 408 of a material, which may be a natural body structure, a contrast agent, a naturally occurring marker, or some other distinguishable distinct physiological, anatomical, or other feature which may be detected. At time $t_2$, the body part 402 contains a distribution 410 which has changed. Changes may be size changes, shape changes, concentration of a detectable material, for example blood, fluid effusion, or a marker or any other detectable material. At time t3, the body part 402 contains a distribution 412 which has changed. Again, changes may be size changes, shape changes, concentration of a detectable material, for example blood, fluid effusion, or a marker or any other detectable material. The optical wavelength may be used to select for particular materials.

As illustrated in FIG. 15B, the techniques described in the present disclosure for image rendering and machine classification/computer aided diagnosis may also be applied to other dimensions than three spatial dimensions, which were described as being useful for diagnosing RA. The number of dimensions may be varied based on, for example, excitation wavelengths, time, level of an external stimulus applied to a body part, a natural process, etc. As mention, also, distributions of detectable properties may evolve over time. Also, other parameters of the OT data acquisition or data features may be changed to create a profile in yet other dimensions respective of the parameter. Light wavelength was mentioned. In embodiments, OT data may distributed over dimensions other than spatial dimensions. These dimensional data may be used independently or combined with spatial dimensions to obtain features for application to a classifier as described above. For example, one spatial dimension $x_2$ may be collapsed by projection (as described in examples above) onto a plane of the other spatial dimension $x_1$ vs. time to form a feature for a classification. The other examples of feature extraction discussed above may be applied to form other features which may be used alternatively or together in any combination to form additional embodiments.

Although in the embodiments disclosed above, the instrumentation for OT acquisition is described according to the assumption that light laser is applied by a scanner through free space. But OT transducers that use fibers may also be used. These locate the points of light injection and light reception by positioning fibers in contact with the skin. In such instruments, the control parameters are varied according to known principles. Such types of OT system may also be used in connection with features of the present disclosure. In addition, features of the classification process may be used with other types of medical imaging.

Figure 16:
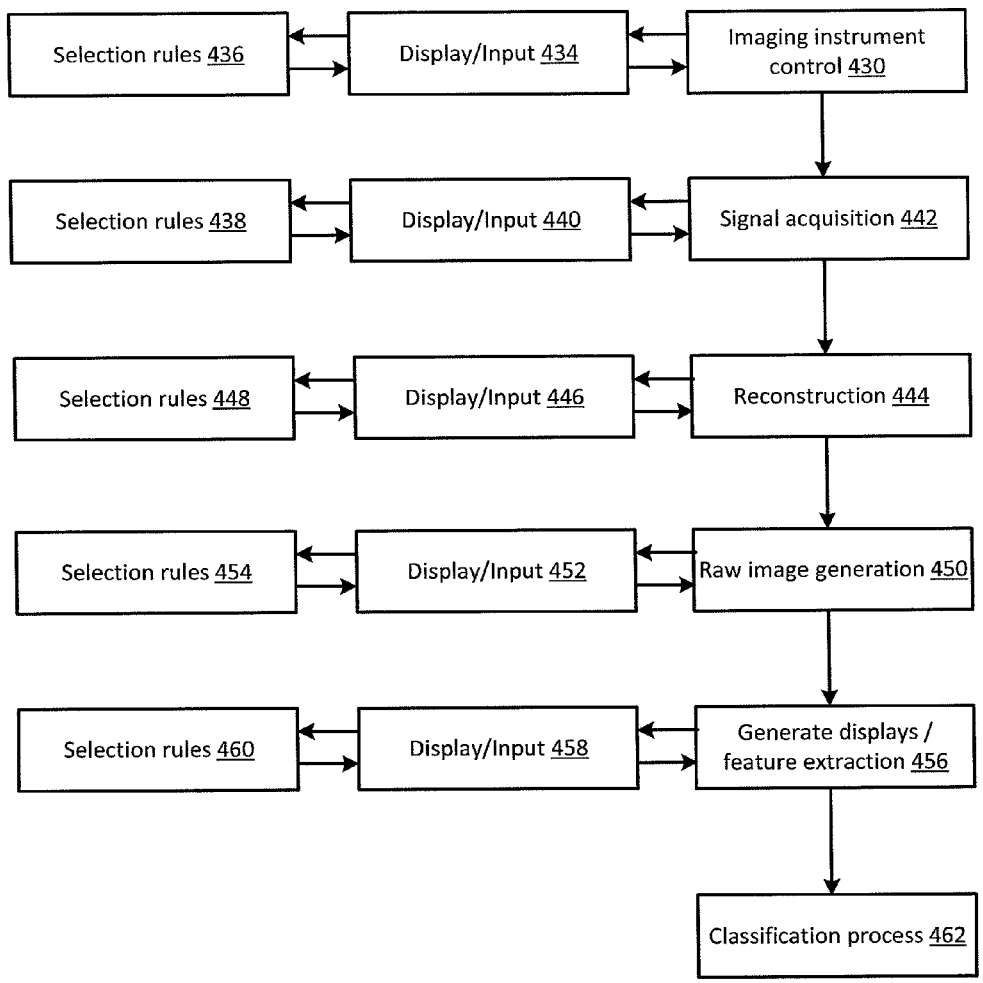
FIG. 16 shows a process for obtaining data for application to a classifier of for rendering output without classification, such as image renderings.

FIG. 16 shows a process for obtaining data for application to a classifier, and/or for rendering output without classification, such as image renderings. For example, OT data may be rendered according to variety of representation forms and many of the classifiers can be imaged directly. For example, the time evolution or spectral density function may rendered as a figure such as a graph. In a first process 430, which may precede final display of OT data or classification (See process 462), an imaging instrument, such as an imaging instrument may be controlled according to parameters entered or adjusted by a user through a user interface as indicated at 434. Default or recommended parameters of the data acquisition phase may be stored, and/or rules for setting parameters (as indicated at 436) may be stored in a non-volatile data store and established as preferred parameters in the user interface or applied automatically to the imaging instrument control (thereby eliminating process 434).

The imaging instrument may be, for example, as described with respect to FIG. 1, 2A, 2E, or 2F may be used or any other suitable device. The parameters of the imaging acquisition process control may include, for example, control the location of laser scan (or the source fibers to use for optical fiber based transducer systems, etc.), the modulation frequency to use, the laser wavelength to use, the finer to scan (or breast to scan, etc.), the length of data collection time, and other parameters. For surface geometry detection, the resolution or accuracy of the surface scan may be controlled, the length of surface geometry scan, and other parameters may be established and used to acquire the respective data.

In process 442, the signal acquisition is performed and may be controlled according to the same principles. That is, user input may be applied, including outputting 440 relevant information and applying default or suggested parameters or ranges from a data store according to rules or values stored therein 438 and including accepting corresponding user commands 440. In process 442, for example, the sensitivity of CCD camera (or light capture apparatus), adjustments to filtering of light, and electrical filtering of CCD image signal, and other parameters may be established.

In process 444, the raw image signal is processed using the processes described herein or using other suitable processes. The parameters that may be set according to processes 466 and 448 may include mesh type and mesh parameters to use to discretize the geometry, the number of mesh elements for the volume or section geometry, mesh voxels, and the type of mesh (e.g., structured vs unstructured mesh.

In process 450, a reconstruction process results in a volumetric or sectional model, which may include dimensions such as time, other parameters, as discussed above with regard to FIGS. 15A and 15B. In this process, parameters that may be controlled in processes 452 and 454 include the light propagation model to use, for example, such as diffusion equation or transport equation and optimization parameters such as tolerance parameters. The user interface may also receive output that indicates a quality of the reconstruction to allow parameters to be altered to refine the quality of the reconstruction. For this purpose, intermediate renderings of features and/or displays representing the reconstruction may output in the display/input process 452.

In process 456, including support processes 458 and 460, optionally, data is converted from unstructured property data to structured property data. The parameters for this conversion, may include, for example, structured voxel size. Final output may be provided as part of process 456. The data may subsequently be applied to a classifier under user control which may include entering the process 200 of FIG. 2B at process 295.

In any of the above examples, the output and receipt of commands from a user may be bypassed as discussed above so that rules or values for parameter setting may be done automatically according to the system implementation.

It will be appreciated that the modules, processes, systems, and sections described above can be implemented in hardware, hardware programmed by software, software instruction stored on a non-transitory computer readable medium or a combination of the above. For example, a method for indicating a maintenance operation can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of ventilation control and/or computer programming arts.

Although the examples described above related to diagnosis of rheumatoid arthritis in a finger joint, the devices, systems, and methods described may be used to diagnose other diseases and conditions in any of a variety body parts.

Moreover, embodiments of the disclosed method, system, and computer program product can be implemented in software executed on a programmed general purpose computer, a special purpose computer, a microprocessor, or the like.

The foregoing merely illustrates the principles of the exemplary embodiments of the present disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the present disclosure and are thus within the spirit and scope of the present disclosure.

What is claimed is:

1. A method of classifying, with respect to a predefined disease, an optical tomographic image of a living sample tissue, comprising:
   scanning light into tissue samples and capturing trans-illumination data from the tissue samples;
   using optical tomographic imaging to generate a first set of images of the tissue samples from the trans-illumination data, including diseased tissue samples having the predefined disease and healthy tissue samples not having the predefined disease;
   extracting, from the first set of images, a plurality of features selected from the group consisting of volumetric features and projection dependent features, the features representing optical properties of a sample tissue;
   statistically analyzing each of the features and selecting responsively to a result of the statistically analyzing, a subset of the features that provides greater predictive accuracy as to the presence of the disease than other features when applied to a predefined classifier;
   scanning light into further tissue samples and capturing further trans-illumination data from the further tissue samples;
   using optical tomographic imaging to generate a second set of images of the further tissue samples from the further trans-illumination data; and
   using the subset of features with the predefined classifier to classify the further tissue samples as having the having the predefined disease or not having the predefined disease based on the second set of images,
   wherein the images in the first and second sets include, for each tissue sample, multiple structured images combined into a planar image from which the at least one of the features is extracted.

2. The method of claim 1, wherein the statistically analyzing includes applying an evolution algorithm in which an initial feature combination is chosen as the first generation parents; all possible mutants are generated by adding, dropping, or replacing one feature from the parent combination; of all the mutants and their parent, the combination with the highest Youden index become the parent in next generation; and repeating until the Youden index stops improving.

3. The method of claim 1, further comprising reconstructing at least one image of optical parameters of the tissue.

4. The method of claim 3, wherein the reconstructing includes reconstructing raw absorption and scattering data as at least one three-dimensional image of absorption and scattering coefficients in the tissue.

5. The method of claim 4, wherein the reconstructing of the three-dimensional image of absorption and scattering coefficients in the tissue includes a prediction model of transmission data exiting from the tissue.

6. The method of claim 5, wherein the prediction model of transmission data includes solving at least one frequency-domain equation of radiative transfer.

7. The method of claim 6, wherein the solution of at least one frequency-domain equation of radiative transfer includes establishing at least one partially-reflective boundary condition.

8. The method of claim 4, wherein the reconstructing of the three-dimensional image of absorption and scattering coefficients in the tissue includes a model-based iterative image reconstruction algorithm.

9. The method of claim 8, wherein the reconstruction includes using at least one transmission data normalized to a sum of each detection point over all illumination points.

10. The method of claim 8, wherein the reconstruction includes using a PDE constrained sequential quadratic programming (SQP) algorithm.

11. The method of claim 10, wherein using a PDE-constrained SQP algorithm includes a preconditioning of a Hessian matrix.

12. The method of claim 11, wherein the preconditioning of the Hessian matrix includes a linear coordinates transformation (LCT) of absorption and scattering coefficients in the tissue.

13. The method of claim 12, wherein the reconstruction of the PDE-constrained SQP algorithm includes assigning values of 0.3 cm' and 8 cm' as an initial guess of absorption and scattering coefficients, respectively, in the tissue.

14. The method of claim 4, wherein the reconstructing of the three-dimensional data of absorption and scattering coefficients in the tissue includes an unstructured computation mesh of the tissue.

15. The method of claim 3, further comprising reconstructing hemoglobin concentration and/or oxygen saturation as a three-dimensional image of optical parameter coefficients in the tissue.

16. The method of claim 3, wherein reconstructing the at least one image of optical parameters includes using at least one transmission data normalized to a sum of all detection points over all illumination points, divided by the total number of measurements.

17. The method of claim 16, wherein the reconstructing includes using a preconditioning of a gradient or Hessian matrix, which makes the image reconstruction process numerically more stable.

18. The method of claim 17, wherein the preconditioning of the gradient or Hessian matrix includes a linear transformation of variables (LTV) for the reconstruction parameters.

19. The method of claim 3, wherein the reconstructing includes using a generalized radial basis function (RBF) based smoothing operator that eliminates "grid effects" due to variation in the cell size of unstructured grids.

20. The method of claim 1, wherein the predefined disease is rheumatoid arthritis.

21. The method of claim 1, wherein the planar image is a projection of a three-dimensional optical property map.

22. The method of claim 1, wherein at least one of the features is a mixture model.

23. The method of claim 22, wherein the at least one of the features is a Gaussian mixture model.

24. The method of claim 22, wherein the at least one of the features is multiple components of a Fourier decomposition of the planar image.

25. The method of claim 1, wherein the planar image is generated from a structured set of raw images representing optical property maps of transverse, sagittal, or coronal sections through a tissue sample projected on a two-dimensional surface.

26. The method of claim 1, wherein the first set of images represent absorption or scattering coefficients derived from frequency domain diffuse optical tomography and the features include ones derived from the first set of the images by parameterization of curvilinear function fits.

27. The method of claim 1, wherein the first set of images represent absorption or scattering coefficients derived from frequency domain diffuse optical tomography and the features include spectral coefficients derived from the first set of images.

28. The method of claim 1, wherein the first set of images represent absorption or scattering coefficients derived from frequency domain diffuse optical tomography and the features include modulation frequencies used to derive the first set of images.

29. The method of claim 1, wherein the first set of images represent at least one of oxy-hemoglobin concentration, deoxy-hemoglobin concentration, total blood volume, and oxygen saturation derived from frequency domain diffuse optical tomography and the features include features derived from the first set of images by parameterization of curvilinear function fits.

30. The method of claim 1, wherein the predefined classifier includes one of a nearest neighbor method (KNN), a discriminate analysis (DA), a support vector machine (SVM) method and a self-organizing maps (SOMs) method.

31. An apparatus that classifies, with respect to a predefined disease, an optical tomographic image of a living sample tissue, the apparatus comprising:
  a processor programmed to implement a classifier based on data obtained by
    scanning light into tissue samples and capturing trans-illumination data from the tissue samples,
    using optical tomographic imaging to generate a first set of images of the tissue samples from the trans-illumination data, including diseased tissue samples having the predefined disease and healthy tissue samples not having the predefined disease,
    extracting, from the first set of images, a plurality of features selected from the group consisting of volumetric features and projection dependent features, the features representing optical properties of a sample tissue, and
    statistically analyzing each of the features and selecting responsively to a result of the statistically analyzing, a subset of the features that provides greater predictive accuracy as to the presence of the disease than other features when applied to a predefined classifier;
  a scanning light source that scans further light into further tissue samples; and
  a photodetector that captures further trans-illumination data from the further tissue samples;
  wherein the processor is further programmed to
    use optical tomographic imaging to generate a second set of images of the further tissue samples from the further trans-illumination data, and
    use the subset of features with the predefined classifier to classify the further tissue samples as having the having the predefined disease or not having the predefined disease based on the second set of images,
    wherein the images in the second set includes, for each tissue sample, multiple structured images combined into a planar image from which the at least one of the features is extracted.

* * * * *